United States Patent
Höcker

(10) Patent No.: US 8,447,536 B2
(45) Date of Patent: May 21, 2013

(54) MEDIUM DENSITY MEASURING SYSTEM

(75) Inventor: Rainer Höcker, Waldshut (DE)

(73) Assignee: Endress + Hauser Flowtec AG, Reinach (CH)

( * ) Notice: Subject to any disclaimer, the term of this patent is extended or adjusted under 35 U.S.C. 154(b) by 431 days.

(21) Appl. No.: 12/216,103

(22) Filed: Jun. 30, 2008

(65) Prior Publication Data

US 2009/0038406 A1  Feb. 12, 2009

Related U.S. Application Data

(60) Provisional application No. 60/929,532, filed on Jul. 2, 2007, provisional application No. 60/929,529, filed on Jul. 2, 2007, provisional application No. 60/929,530, filed on Jul. 2, 2007, provisional application No. 60/929,531, filed on Jul. 2, 2007.

(30) Foreign Application Priority Data

| Jun. 30, 2007 | (DE) | 10 2007 030 690 |
| Jun. 30, 2007 | (DE) | 10 2007 030 691 |
| Jun. 30, 2007 | (DE) | 10 2007 030 699 |
| Jun. 30, 2007 | (DE) | 10 2007 030 700 |

(51) Int. Cl.
  *G01L 7/00* (2006.01)
(52) U.S. Cl.
  USPC .......... 702/50; 702/23; 702/35; 702/45; 702/104; 702/137
(58) Field of Classification Search
  USPC .......... 702/23, 35, 45, 50, 104, 137; 73/23.2, 73/30.01
  See application file for complete search history.

(56) References Cited

U.S. PATENT DOCUMENTS

| 6,505,519 B2* | 1/2003 | Henry et al. ............ 73/861.356 |
| 6,550,327 B1* | 4/2003 | Van Berk .................. 73/438 |
| 6,681,189 B1 | 1/2004 | Morrison |
| 7,065,427 B1* | 6/2006 | Dakshina-Murthy et al. ............... 700/120 |
| 7,212,928 B2* | 5/2007 | Cook et al ................ 702/45 |
| 2004/0049358 A1* | 3/2004 | Cook et al. ............... 702/45 |
| 2005/0034535 A1 | 2/2005 | Sprague |
| 2005/0043900 A1 | 2/2005 | Franda |
| 2006/0025955 A1 | 2/2006 | Kurtz |

FOREIGN PATENT DOCUMENTS

| CN | 168 7715 A | 10/2005 |
| DE | 3624093 A1 | 1/1988 |
| DE | 100 44 491 A1 | 4/2002 |

(Continued)

OTHER PUBLICATIONS

International Search Report (FL0391).

(Continued)

Primary Examiner — Elias Desta
(74) Attorney, Agent, or Firm — Bacon & Thomas, PLLC

(57) ABSTRACT

A measuring system for the precise measuring a density of a medium, flowing in a line. compressible. The measuring system comprises: a temperature sensor and a pressure sensor. Both sensors communicate with a measuring electronics of the system.

The measuring electronics are operable to provide, based on temperature measurement and pressure measurement signal, density measured-value representing, instantaneously, a local density, of the flowing medium at a virtual density measuring point, predeterminably spaced from the pressure measuring point and/or from the temperature measuring point, along the flow axis.

47 Claims, 4 Drawing Sheets

FOREIGN PATENT DOCUMENTS

| | | |
|---|---|---|
| EP | 0 364 217 A2 | 4/1990 |
| EP | 0 454 230 A2 | 10/1991 |
| EP | 0 666 468 A2 | 8/1995 |
| GB | 1 317 344 | 5/1972 |
| GB | 2 079 465 A1 | 1/1982 |
| WO | WO 99/09388 | 2/1999 |
| WO | WO 99/56091 | 11/1999 |
| WO | WO 00/14484 | 3/2000 |
| WO | WO 01/66955 A2 | 9/2001 |
| WO | WO 2004/023081 A2 | 3/2004 |
| WO | WO 2004/038344 A1 | 5/2004 |

OTHER PUBLICATIONS

International Search Report (FL0392).
International Search Report (FL0393).
International Search Report (FL0394).
English translation of IPR (FL0391).
English translation of IPR (FL0392).
English translation of IPR (FL0393).
English translation of IPR (FL0394).
NL—International Search Report (FL0391-WO) issued on Jan. 21, 2009 (International Appl. PCT/EP2008/058319).
NL—International Search Report (FL0392-WO) issued on Dec. 23, 2008 (International Appl. PCT/EP2008/058320).
NL—International Search Report (FL0393-WO) issued on Nov. 26, 2008 (International Appl. PCT/EP2008/058321).
NL—International Search Report (FL0394-WO) issued on Mar. 2, 2010 (International Appl. PCT/EP2008/058326).
CH—English translation of IPR (FL0391-WO) Mar. 2, 2010 (International Appl. PCT/EP2008/058319).
CH—English translation of IPR (FL0392-WO) issued on Mar. 2, 2010 (International Appl. PCT/EP2008/058320).
CH—English translation of IPR (FL0393-WO) issued on Feb. 9, 2010 (International Appl. PCT/EP2008/058321).
CH—English translation of IPR (FL0394-WO) issued on Dec. 5, 2008 (International Appl. PCT/EP2008/058326).

* cited by examiner

MEDIUM DENSITY MEASURING SYSTEM

CROSS-REFERENCE TO RELATED APPLICATIONS

This application is a nonprovisional application based on the following U.S. provisional applications: U.S. provisional application No. 60/929,532, filed on Jul. 2, 2007; U.S. provisional application 60/929,529, filed on Jul. 2, 2007; on U.S. provisional application 60/929,530, filed on Jul. 2, 2007; and on U.S. provisional application 60/929,531, filed on Jul. 2, 2007; and priority is also claimed on the following German applications: on German application 10 2007 030 700.6 filed on Jun. 30, 2007; on German application 10 2007 030 690.5, filed on Jun. 30, 2007; on German application 10 2007 030 699.9 filed on Jun. 30, 2007; and on German application 10 2007 030 691.3 filed on Jun. 30, 2007.

TECHNICAL FIELD

The invention relates to a measuring system for measuring a density of a medium variable with respect to a thermodynamic state, especially at least partly compressible, flowing in a process line, such as a process pipeline or tube, along a flow axis of the measuring system. The measuring system measures by means of a temperature sensor, a pressure sensor and a measuring electronics communicating, in each case, at least at times, with the temperature sensor and the pressure sensor, and producing, at least at times, at least one density measured-value representing, as accurately as possible, a local density of the flowing medium.

BACKGROUND DISCUSSION

For registering process-describing, measured variables of flowing media, such as the thermodynamic state variable, density, or measured variables derived therefrom, and for producing measured-values correspondingly representing such measured variables, industrial process measurements technology applies measuring systems installed near to the process. This is done especially also in connection with the automation of chemical processes or processes involving adding value to materials. These measuring systems are often composed of two or more, discrete, measuring, field devices, which communicate with one another and are each arranged directly at, on or in a process line, through which the medium flows. The measured variables to be registered can include, besides density, for example also other thermodynamic state variables, especially such variables as are registerable by sensor and, as a result, directly measurable, such as e.g. pressure or temperature, directly or indirectly measurable flow parameters, such as e.g. a flow velocity, a volume flow, e.g. a volume flow rate, or a mass flow, e.g. a mass flow rate, or other complex transport variables, such as e.g. a heat flux, as well as also other measured variables specific to the medium, such as e.g. a viscosity, of an at least partly liquid, powdered or gaseous medium conveyed in a process line embodied, for example, in the form of a pipeline.

Especially for the indirect (in the following, thus, also referred to as virtual) measurement of density, based on pressure and temperature measurement signals generated by means of corresponding sensors, as well as also measured variables possibly derived therefrom, for example mass flow or volume flow, a large number of industrial standards have become established, which recommend a largely standardized, and, thus, comparable, calculation, especially also with application of directly registered and, thus, actually measured temperatures and/or pressures, and which find application as a function of application area and medium. Examples of such standards include, by way of example, the industrial standard "IAWPS Industrial Formulation 1997 for the Thermodynamic Properties of Water and Steam", International Association for the Properties of Water and Steam (IAWPS-IF97), "A.G.A. Manual for the Determination of Supercompressibility Factors for Natural Gas—PAR Research Project NX-19", American Gas Association (AGA-NX19, Library of Congress No. 63-23358), the international standard ISO 12213:2006, Part 1-3 "Natural gas—Calculation of compression factor", as well as also the therein cited A.G.A. Compressibility Factors for Natural Gas and Other Related Hydrocarbon Gases", American Gas Association Transmission Measurement Committee Report No. 8 (AGA-8) and "High Accuracy Compressibility Factor Calculation for Natural Gases and Similar Mixtures by Use of a Truncated Viral Equation", GERG Technical Monograph TM2 1998 & Fortschritt-Berichte VDI (Progress Reports of the Association of German Engineers), Series 6, No. 231 1989 (SGERG-88).

Often, the ascertaining of density can also serve for converting a directly measured, mass flow into an, as a result, indirectly or virtually measured, volume flow, or vice versa. For direct measurement of flow parameters serving as primary measured variables therefor—thus, for example, a local flow velocity, a local volume flow, or a local mass flow—measuring systems of the type being discussed include at least one corresponding flow sensor, which, by reacting at least predominantly to a flow parameter primarily to be registered for the flowing medium, or also to changes of the same, delivers, during operation, at least one measurement signal, especially an electrical measurement signal, correspondingly influenced by the measured variable primarily to be registered and representing such as accurately as possible. The at least one flow sensor can, in such case, be embodied to contact the medium, at least partially, for example by being immersed therein, or to measure externally through the wall of the process line or a membrane, or diaphragm. Usually, the flow sensor is provided, in such case, by means of a, most often, very complex flow transducer, which is inserted appropriately directly into the process line, or into a bypass, conveying the medium.

Marketed flow transducers are usually implemented as pre-fabricated, pre-calibrated units equipped with a carrier tube insertable into the course of the pertinent process line and also with at least one physical-to-electrical converting element appropriately pre-assembled therewith. This converting element, possibly in conjunction with the carrier tube itself and/or other components of the flow transducer, especially passive-invasive components, such as e.g. flow obstacles protruding into the flow and/or active components of the flow transducer, such as e.g. a coil arrangement placed externally on the support tube for generating a magnetic field, or sound producing units, forms the at least one flow sensor delivering the measurement signal. Widely distributed in industrial measurements technology are, especially, magneto-inductive flow transducers, flow transducers evaluating the travel time of ultrasonic waves coupled into flowing media, eddy flow transducers, especially vortex flow transducers, flow transducers with oscillating measuring tubes, flow transducers making use of pressure differences, or thermal flow-measuring transducers. Principles of construction and functioning of magneto-inductive flow transducers are described e.g. in EP-A 1 039 269, U.S. Pat. Nos. 6,031,740, 5,540,103, 5,351,554, 4,563,904, while such for ultrasonic flow transducers appear e.g. in U.S. Pat. Nos. 6,397,683, 6,330,831, 6,293,156, 6,189,389, 5,531,124, 5,463,905, 5,131,279, 4,787,252. Since also the others of the aforementioned principles of measurement usually put into practice in industrial flow measuring transducers are likewise sufficiently known to those skilled in the art, a further explanation of these and other principles of measurement established in industrial measurements technology and implemented by means of flow measuring transducers can be omitted here.

Industrial measuring systems registering flow parameters involve, often, those, in the case of which, at least one of the measuring points delivering the actual measurement signals and thus, in the following, referred to as real, is formed by means of a compact inline measuring device having a flow transducer of the aforementioned kind. Further examples for such measuring systems, especially measuring systems formed by means of compact, inline measuring devices with flow transducers known per se to those skilled in the art, are presented, additionally, in detail in, among others, EP-A 605 944, EP-A 984 248, EP-A 1 767 908, GB-A 21 42 725, U.S. Pat. Nos. 4,308,754, 4,420,983, 4,468,971, 4,524,610, 4,716, 770, 4,768,384, 5,052,229, 5,052,230, 5,131,279, 5,231,884, 5,359,881, 5,458,005, 5,469,748, 5,687,100, 5,796,011, 5,808,209, 6,003,384, 6,053,054, 6,006,609, 6,352,000, 6,397,683, 6,513,393, 6,644,132, 6,651,513, 6,651,512, 6,880,410, 6,910,387, 6,938,496, 6,988,418, 7,007,556, 7,010,366, US-A 2002/0096208, US-A 2004/0255695, US-A 2005/0092101, US-A 2006/0266127, WO-A 88/02 476, WO-A 88/02 853, WO-A 95/08758, WO-A 95/16 897, WO-A 97/25595, WO-A 97/46851, WO-A 98/43051, WO-A 00/36 379, WO-A 00/14 485, WO-A 01/02816, WO-A 02/086 426, WO-A 04/023081 or WO-A 04/081500, WO-A 05/095902, as well as also in the not pre-published applications DE 102006034296.8 and 102006047815.0 of the assignee.

For the further processing or evaluation of measurement signals produced in the measuring systems, such additionally include at least one corresponding measuring electronics. The measuring electronics, communicating in suitable manner with the pertinent measuring transducer, especially also with the at least one converting element, produces during operation, with application of the at least one measurement signal, repeatedly, at least one measured-value instantaneously representing the measured variable, thus, for example, a mass flow measured-value, volume flow measured-value, a density measured-value, a viscosity measured-value, a pressure measured-value, a temperature measured-value, or the like. The measured-values, especially the indirectly, or also virtually, measured, density measured-value, are, in such case, often ascertained by means of highly complex calculations according to one of the mentioned industry standards, for example "AGA 4", "AGA 8", "AGA-NX19", "IAWPS-IF97", "SGERG-88", or the like.

For accommodating the measuring electronics, such measuring systems include, most often, a corresponding electronics housing, which, as proposed e.g. in U.S. Pat. No. 6,397, 683 or WO-A 00/36 379, can be arranged remotely from the measuring transducer and connected with such via a flexible cable. Alternatively thereto or in supplementation thereof, the electronics housing can, however, also, as shown, for example, in EP-A 903 651 or EP-A 1 008 836, be arranged directly on the measuring transducer or on a measuring transducer housing separately housing the measuring transducer, in order to form a compact, inline measuring device, for example a Coriolis mass flow/density measuring device, an ultrasonic flow-measuring device, a vortex flow-measuring device, a thermal flow-measuring device, a magneto-inductive flow-measuring device, or the like. In the case in which the electronics housing is arranged on a measuring transducer housing, the electronics housing serves, as shown, for example, in EP-A 984 248, U.S. Pat. Nos. 4,716,770 or 6,352, 000, often also for accommodating some mechanical components of the measuring transducer, such as e.g. elements deforming during operation on the basis of mechanical effects, elements such as membrane, rod, sleeve or tubular deformation- or vibration-elements; compare, in this connection, also the U.S. Pat. No. 6,352,000 mentioned above.

In the case of measuring systems of the described kind, the measuring electronics is usually electrically connected via electrical lines, and/or wirelessly by radio, with a superordinated, electronic, data processing system arranged, most often, spatially remotely, and also spatially distributed, from the measuring electronics. To this data processing system are forwarded, in near-time, the measured-values produced by the measuring system. The measured-values are forwarded by means of measured-value signals carrying the measured-values. Measuring systems of the described kind are, additionally, usually, by means of a data transmission network (wired- and/or radio-based) provided within the superordinated data processing system, connected together and/or with corresponding electronic process controls, for example programmable logic controllers (PLCs) installed on-site or process control computers installed in a remote control room, where the measured-values produced by means of the measuring system and digitized in suitable manner and correspondingly encoded are sent. By means of process control computers, with application of correspondingly installed software components, the transmitted measured-values can be further processed and visualized as corresponding measurement results e.g. on monitors and/or converted into control signals for other field devices, such as e.g. magnetically operated valves, electric motors, etc., embodied as actuators for process control. Accordingly, the data processing system serves usually also for conditioning the measured-value signal delivered from the measuring electronics corresponding to the requirements of downstream data transmission networks, for example suitably digitizing such and, on occasion, converting it into a corresponding telegram, and/or evaluating it on-site. For such purposes, provided in these data processing systems, electrically coupled with the pertinent connection lines, are evaluating circuits, which pre- or further-process, and, if required, suitably convert, measured-values received from the measuring electronics. Serving for data transmission in such industrial data processing systems, as least sectionally, are, especially serial, fieldbuses, such as e.g. FOUNDATION FIELDBUS, CAN, CAN-OPEN, RACK-BUS-RS 485, PROFIBUS, etc. or, for example, also networks based on the ETHERNET standard, as well as the corresponding standardized transmission protocols, which are, most often, independent of application.

Usually, it is possible to implement by means of control computers, besides such process visualization, monitoring and control, also remote servicing, parametering and/or monitoring of the connected measuring system. Accordingly, measuring electronics of modern, measuring, field devices permit, besides actual measured-value transmission, also transmission of various setting- and/or operating-parameters used in the measuring system, such as e.g. calibration data, measured-value ranges and/or also diagnostic values ascertained internally in the field devices. In support of this, operating data intended for the measuring system can, most often, likewise be sent via the aforementioned data transmission networks, which are, most often, hybrid as regards transmission physics and/or transmission logic.

Besides the evaluating circuits required for processing and converting measured-values delivered from connected measuring electronics, superordinated data processing systems of the described kind include, most often, also electrical supply circuits serving for supplying the connected measuring electronics and, as a result, also the pertinent measuring system with electrical energy, or power. The supply circuits provide for the pertinent measuring device electronics an appropriate supply voltage, which is, on occasion, fed directly by the connected fieldbus, and drive the electrical lines connected to the measuring device electronics, as well as the electrical currents flowing therethrough. A supply circuit can, in such case, for example, be assigned to exactly one measuring electronics and accommodated together with the evaluating circuit associated with the particular measuring device, for example joined to form a corresponding fieldbus adapter, in a housing common to both, embodied e.g. as a top-hat rail module. It is, however, also quite usual to accommodate such superordinated evaluating circuits and supply circuits, in each case, in separate housings, on occasion spatially removed from one another and to wire them appropriately together via external cables.

In the case of industrial measuring systems of the type being discussed here, often involved, as a result, are spatially distributed measuring systems, wherein, in each case, a plurality of measured variables of equal and/or different type are locally registered by sensors at real, mutually separated measuring points along a flow axis of the measuring system defined by the process line. These measured variables are fed to the common measuring electronics in the form of corresponding, electrical, measurement signals by wire, for example also in the so-called HART®-MULTIDROP-method or also in the so-called burst-mode method, and/or wirelessly, especially by radio and/or optically, on occasion also encoded into a digital signal or in a digitally transmitted telegram. For the case described above, in which such a measuring system is formed by means of a flow transducer, it is thus possible, for example in addition to the at least one, practically directly registered, flow parameter serving as primary measured variable, for example the volume flow, to ascertain, at least indirectly and, as a result, to measure, by means of the same measuring electronics, at least virtually, with application also of other, remotely registered, measured variables, for example, a remote, local temperature or a remote, local pressure in the medium, also derived, secondary measured variables, such as e.g. a mass flow and/or a density.

Experimental investigations on distributed measuring systems of the type being discussed, which, as shown e.g. also in U.S. Pat. No. 6,651,512, ascertain, by means of a directly measured, volume flow and a virtually measured density, a mass flow as an indirectly measured variable, have shown that, especially also despite application of internally, as well as externally, ascertained, measured variables proved to be very precise in the measuring ranges usual for the pertinent caliber of the process line, significant errors can arise in the result of a measurement virtual in the above sense. It is quite possible for these errors to lie in the range of about 5% of the actual measured variable or even beyond. This is the case, especially also when ascertaining measured variables, such as e.g. volume flow, temperature or pressure, as intermediate, really measured variables, and/or density as an intermediate variable measured virtually according to measuring and calculating methods recommended in the aforementioned industrial standards.

Further, comparative investigations have, in such case, additionally shown that the aforementioned measurement errors can show, among other things, a certain dependence on the instantaneous Reynolds number of the flow, as well as also on the instantaneous thermodynamic state of the medium. However, it has also been found, in this connection, that, in numerous industrial applications, especially those involving compressible and/or at least 2-phase media, the Reynolds number, or the thermodynamic state of the medium, can be not only chronologically but also spatially variable to a high degree, especially in the direction of the flow axis of the measuring system. Besides applications having at least partially compressible media, additionally especially also applications show a significant transverse sensitivity to spatial variances of the Reynolds number, or the thermodynamic state, when the measurement of at least one of the measured variables occurs at a measuring point (real or virtual), at which the process line has a caliber deviating at least from one of the measuring points (real or virtual) to the other. This is e.g. the case in the application of flow conditioners reducing the cross section of the line (such as in the case of e.g. nozzles serving as so-called reducers), which can find application in the inlet region of flow measuring transducers, or also in the application of flow conditioners increasing the cross section of the line (so-called diffusers) in the outlet region of flow measuring transducers. Measuring systems with such reducers and/or diffusers are described, for example, in GB-A 21 42 725, U.S. Pat. No. 5,808,209, US-A 2005/0092101, U.S. Pat. Nos. 6,880,410, 6,644,132, 6,053,054, 6,644,132, 5,052, 229 or 6,513,393 and are used, for example, for improving accuracy of measurement of flow measuring transducers. It has, in such case, been further ascertained that such transverse sensitivities based on application of reducers and/or diffusers are significant for caliber ratios between about 0.6 and 0.7, while their influence for caliber ratios with extreme diameter jumps of smaller than 0.2 are quite negligible.

Another application area having a significant sensitivity to the aforementioned variances as affecting the desired accuracy of measurement concerns, furthermore, those measuring systems, which are provided for the flow measurement of heavy gases, such as, perhaps, carbon dioxide or also phosgene, or long-chain carbon compounds having a molecular wa of over 30 g/mol.

The above-described spatial variance of the Reynolds number can, in turn, lead to the fact that practically each of the aforementioned, mutually spaced, real measuring points of the distributed measuring system has, during operation, a local Reynolds number deviating, to a considerable degree, from the local Reynolds number of each of the other, also-used, measuring points. Equally, also the mentioned variance of the thermodynamic state would lead to the fact that mutually spaced, measuring points of the distributed measuring system can have thermodynamic states differing from one another. In view of this, thus, each of the measured variables, as measured on a distributed basis, would have to be adjusted according to the particularly associated, local Reynolds number and/or the particularly associated, local thermodynamic state, a task which, in the absence of the information required therefor, namely the, in each case, other, but remotely measured, state variables, is not directly possible. If, for example, the density and/or the mass flow, calculated on the basis of the measured state variables pressure and temperature, would be calculated without taking into consideration the variance of the Reynolds number, or thermodynamic state, an additional measurement error would result, having essentially a quadratic dependence on the flow velocity. Accordingly, for the aforementioned configuration, at flow velocities of clearly less than 10 m/s, the measuring accuracy of about 0.1% to 0.5%, currently strived for, is practically no longer significant.

Starting from the above-described disadvantages of measuring systems of the described kind, especially those ascertaining a mass flow or a volume flow, an object of the invention is to increase the accuracy of measurement for such secondary measured variables ascertained with application of spatially, distributedly registered, thermodynamic state variables such as pressure and/or temperature.

For achieving the object, the invention resides in a measuring system for measuring a density of a medium, which is variable as regards a thermodynamic state, especially at least partially compressible, flowing in a process line along a flow axis of the measuring system. The measuring system includes therefor: At least one temperature sensor placed at a temperature measuring point, reacting primarily to a local temperature, $\Theta$, of medium flowing past, and delivering at least one temperature measurement signal influenced by the local temperature of the medium to be measured; at least one pressure sensor placed at a pressure measuring point, reacting primarily to a local pressure, p, especially a static pressure, of medium flowing past, and delivering at least one pressure measurement signal influenced by the local pressure, p, in the medium to be measured; and a measuring electronics communicating, in each case, at least at times, with at least the temperature sensor and the pressure sensor, and producing, at least at times, with application both of the temperature measurement signal and also at least the pressure measurement signal, at least one density measured-value, especially a digital density measured-value representing, instantaneously, a local density, $\rho$, of the flowing medium at a virtual, density measuring point, especially a locationally fixed, virtual, density measuring point, predeterminably spaced from the pressure measuring point and/or the temperature measuring point along the flow axis.

In a first embodiment of the invention, it is provided that the measuring electronics includes a data memory, especially a non-volatile data memory, which stores, at least at times, at least one measuring system parameter specifying solely the medium currently to be measured, especially a system parameter such as a specific heat capacity, $c_p$, of the medium currently to be measured, a molar mass, n, of the medium and/or the number, f, of degrees of oscillatory freedom of the atoms, or molecules, of the medium, as determined by the molecular structure of the medium.

In a second embodiment of the invention, it is provided that the measuring electronics ascertains the density measured-value with application of the at least one measuring system parameter specifying solely the medium currently to be measured.

In a third embodiment of the invention, it is provided that the measuring electronics includes a data memory, especially a non-volatile data memory, which stores, at least at times, at least one measuring system parameter specifying both the medium to be measured by means of the measuring system as well as also instantaneous circumstances of installation of the measuring system, wherein the circumstances of installation are determined by the arrangement of pressure-, temperature- and density measuring points relative to one another, as well as, in each case, by the form and size of the process line in the areas of the pressure-, temperature- and density measuring points. In a further development of this embodiment of the invention, the measuring electronics ascertains the density measured-value with application of the at least one measuring system parameter specifying both the medium currently to be measured by means of the measuring system as well as also instantaneous circumstances of installation of the measuring system.

In a fourth embodiment of the invention, it is provided that the measuring electronics includes a data memory, especially a non-volatile data memory, which stores, at least at times, at least one measuring system parameter of a first kind specifying the medium currently to be measured, especially a specific heat capacity of the medium currently to be measured, a molar mass of the medium and/or the number of degrees of freedom of the medium, and which stores, at least at times, at least one measuring system parameter of a second kind specifying both the medium currently to be measured as well as also instantaneous circumstances of installation of the measuring system, wherein the instantaneous circumstances of installation are determined by the arrangement of pressure-, temperature- and density-measuring points relative to one another, as well as, in each case, by the form and size of the process line in the regions of the pressure-, density- and/or temperature-measuring points, and wherein the measuring electronics ascertains the density measured-value with application at least of the measuring system parameter of the first kind and the measuring system parameter of the second kind.

In a fifth embodiment of the invention, it is provided that the measuring electronics receives, at least at times, numerical parameter values, especially numerical parameter values ascertained, externally of the measuring system and/or near in time, for at least one measuring system parameter specifying a medium to be measured and/or instantaneous circumstances of installation of the measuring system, especially a heat capacity, $c_p$, for medium to be measured, which represents a specific heat capacity, $c_p$, earlier ascertained and/or measured remotely from the density measuring point for the medium to be measured.

In a sixth embodiment of the invention, it is provided that the measuring electronics communicates, especially via fieldbus, at least at times, especially by wire and/or by radio, with a superordinated, electronic, data processing system. In a further development of this embodiment of the invention, it is additionally provided that the measuring electronics transmits the density measured-value to the data processing system and/or wherein the measuring electronics receives from the data processing system, at least at times, measuring system parameters specifying numerical parameter values for the medium to be measured currently, especially its thermodynamic properties and/or its chemical composition, especially a specific heat capacity, $c_p$, of the medium currently to be measured, a molar mass, n, of the currently to be measured medium and/or the number, f, of degrees of oscillatory freedom of the atoms, or molecules, of the currently to be measured medium, and/or that the measuring electronics is connected with the superordinated, electronic, data processing system by means of a fieldbus, especially a serial fieldbus.

In a seventh embodiment of the invention, it is provided that the measuring electronics ascertains, during operation, at least at times, a specific heat capacity, $c_p$, of the currently to be measured medium, especially on the basis of the formula:

$$c_P = \left(1 + \frac{f}{2}\right) \cdot \frac{R}{n},$$

wherein n is a molar mass, R, the absolute gas constant, with R=8.3143 J/(K mol) and f, a number, determined by the molecular structure of the medium, of degrees of oscillatory freedom of its atoms, or molecules.

In an eighth embodiment of the invention, it is provided that the measuring electronics generates, repetitively, a temperature measured-value, especially a digital temperature measured-value, based on the temperature measurement signal, and wherein the temperature measured-value represents, instantaneously, the temperature of the medium at the temperature measuring point.

In a ninth embodiment of the invention, it is provided that the measuring electronics generates, repetitively, a pressure measured-value, especially a digital pressure measured-value, based on the pressure measurement signal, and wherein the pressure measured-value represents a pressure instantaneously reigning in the medium, especially at the pressure measuring point.

In a tenth embodiment of the invention, it is provided that the measuring system further includes a flow sensor placed at a flow measuring point and reacting, primarily, to a local flow parameter, especially a flow parameter averaged over a cross section of the process line, especially a flow velocity, a volume flow or a mass flow, of the medium to be measured, especially also changes of the same, and wherein the flow sensor delivers at least one flow measurement signal influenced by the local flow parameter.

Developing this embodiment of the invention further, it is provided that
  the measuring electronics communicates, at least at times, also with the flow sensor, and wherein the measuring electronics ascertains the density measured-value with application also of the flow measurement signal; and/or
  the medium has, at the virtual density measuring point, a thermodynamic state corresponding to a thermodynamic state of the medium at the velocity measuring point; and/or
  the virtual density measuring point and the flow measuring point at least partially overlap one another, especially they are coincident; and/or
  the temperature measuring point and the flow measuring point at least partially overlap one another, especially they are coincident; and/or
  the pressure measuring point and the flow measuring point at least partially overlap one another; and/or
  the density measured-value represents a local density of the medium in the region of the flow sensor; and/or
  the measuring electronics communicates with the flow sensor by means of a field bus, especially a serial field bus, and/or wirelessly by radio; and/or
  the measuring electronics communicates, at least at times, with the flow sensor, wherein the measuring electronics ascertains, with application at least of the flow measurement signal, a velocity measured-value, especially a digital flow measured-value, which represents instantaneously the flow velocity of the flowing medium.

In an eleventh embodiment of the invention, it is provided that the measuring electronics produces the density measured-value also with application of at least one numerical compensation factor, especially a digitally stored compensation factor, which corresponds with a locational variability occurring along the flow axis of the measuring system, especially a locational variability ascertained in advance or during operation, of at least one thermodynamic state variable of the medium, especially a temperature, a pressure or a density, and/or with a locational variability occurring along the flow axis of the measuring system, especially a locational variability ascertained in advance or during operation, of the Reynolds number of the flowing medium.

Developing this embodiment of the invention further, it is additionally provided that
  the at least one compensation factor is ascertained taking into consideration the medium actually to be measured, especially its composition and/or its thermodynamic properties, especially during a calibration of the measuring system with known, reference medium and/or during start-up of the measuring system on-site; and/or
  the measuring electronics ascertains a compensation factor, at least once, during start-up of the measuring system; and/or
  the measuring electronics repetitively ascertains the compensation factor during operation of the measuring system, especially in conjunction with a change of at least one chemical property of the medium to be measured or with a replacement of the same with another medium; and/or
  the measuring electronics ascertains the at least one compensation factor on the basis of a predetermined, specific heat capacity, $c_p$, of the current medium, especially a heat capacity ascertained in dialog with a user and/or externally of the measuring electronics; and/or
  the measuring electronics includes a data memory storing the at least one compensation factor, especially a data memory embodied as a table memory and/or a non-volatile memory; and/or
  the data memory stores a plurality of compensation factors ascertained in advance for different media and/or for different circumstances of installation; and/or
  the measuring electronics selects the at least one compensation factor taking into consideration the current medium, as well as the current circumstances of installation, from the plurality of compensation factors stored in the data memory.

In a twelfth embodiment of the invention, it is provided that the measuring electronics produces the density measured-value with application of at least one density correction value ascertained at run time, dependent both on a flow velocity of the medium as well as also on the local temperature reigning at the temperature measuring point, wherein the correction value corresponds with an instantaneous, locational variability of at least one thermodynamic state variable of the medium, especially with such an instantaneous, locational variability related to the medium currently to be measured as well as to instantaneous circumstances of installation and/or with such an instantaneous, locational variability occurring along the flow axis of the measuring system, and/or wherein the correction value corresponds with an instantaneous locational variability of the Reynolds number of the flowing medium, especially with a locational variability of the Reynolds number related to the medium and/or the type of construction of the measuring system, or with an instantaneous variability of the Reynolds number occurring along the flow axis of the measuring system.

Further developing this embodiment of the invention, it is further provided that
  the measuring electronics ascertains, during operation, a velocity measured-value, especially a digital velocity measured-value, representing, instantaneously, the flow velocity of the flowing medium and that the measuring electronics ascertains, with application of the velocity measured-value as well as the temperature measured-value, the density correction value; and/or
  the measuring electronics compares, repetitively, during operation, the density correction value with at least one predetermined reference value; and/or
  the measuring electronics, based on a comparison of density correction value and reference value, quantitatively signals an instantaneous deviation of the density correction value from the reference value and/or generates an alarm, which signals an undesired discrepancy, especially an unallowably high discrepancy, between density correction value and associated reference value.

In a thirteenth embodiment of the invention, it is provided that the measuring electronics, based on the pressure measurement signal, as well as on the temperature measurement signal, ascertains a provisional density measured-value, especially according to one of the industry standards AGA 8, AGA NX-19, SGERG-88 IAWPS-IF97, ISO 12213:2006, representing a density which the flowing medium only apparently has at the virtual density measuring point.

Further developing this embodiment of the invention, it is additionally provided that the measuring electronics ascertains, repetitively during operation, a density error corresponding with a deviation, especially a relative deviation, of the provisional density measured-value from the density measured-value, and especially issues such also in the form of a numerical, density measured-value; and/or the measuring electronics issues an instantaneous density error corresponding with a deviation, especially a relative deviation, of provisional density measured-value and density measured-value, in the form of a numerical, density error value and/or compares the instantaneous density error with at least one predetermined reference value and, based on this comparison, generates, at times, an alarm signaling an undesired, especially impermissibly high, discrepancy between provisional density measured-value and density measured-value.

In a fourteenth embodiment of the invention, it is provided that the measuring system includes, further, at least one flow sensor placed at a flow measuring point and reacting primarily to a local flow parameter, especially a flow parameter averaged over a cross section of the process line, especially a flow velocity, a volume flow or a mass flow of the medium to be measured, especially also to changes of the same, and delivering at least one flow measurement signal influenced by the local flow parameter, wherein the measuring electronics communicates, at least at times, with the flow sensor and wherein the measuring electronics, with application at least of the flow measurement signal, ascertains a volume flow measured-value, especially a digital volume flow measured-value, representing, instantaneously, a volume flow rate of the flowing medium; and/or the measuring electronics ascertains, with application at least of the density measured-value and the volume flow measured-value, a mass flow measured-value, especially a digital mass flow measured-value, representing, instantaneously, a mass flow rate of the flowing medium; and/or wherein the measuring electronics ascertains, with application at least of the temperature measurement signal, the pressure measurement signal and the flow measurement signal, a mass flow measured-value, especially a digital mass flow measured-value, representing, instantaneously, a mass flow rate of the flowing medium; and/or the flow measuring point is arranged upstream of the temperature measuring point and/or upstream of the pressure measuring point; and/or the at least one flow sensor is formed by means of at least one piezoelectric element and/or by means of at least one piezoresistive element; and/or the at least one flow sensor is formed by means at least of an electrical resistance element, especially a resistance element through which a heating current flows, at least at times; and/or the at least one flow sensor is formed by means of at least one measuring electrode tapping electrical potentials, especially a measuring electrode contacting flowing medium; and/or the at least one flow sensor is formed by means of at least one measuring capacitor reacting to changes of the flow parameter; and/or the at least one flow sensor, especially a flow sensor protruding at least partially into a lumen of the process line, is located downstream of at least one bluff body immersed in the medium and protruding into a lumen of the process line.

In a fifteenth embodiment of the invention, it is provided that the measuring electronics communicates with the temperature sensor by means of a fieldbus, especially a serial fieldbus, and/or wirelessly by radio.

In a sixteenth embodiment of the invention, it is provided that the measuring electronics communicates with the pressure sensor by means of a field bus, especially a serial fieldbus, and/or wirelessly by radio.

In a seventeenth embodiment of the invention, it is provided that the medium at the density measuring point is in a thermodynamic state differing, at least at times, significantly, especially to a degree significant for a desired accuracy of the measuring accuracy of the measuring system, as regards at least one local, thermodynamic state variable, especially a temperature and/or a pressure and/or a density, from a thermodynamic state of the medium at the temperature measuring point and/or a thermodynamic state of the medium at the pressure measuring point.

In an eighteenth embodiment of the invention, it is provided that the flowing medium has a Reynolds number greater than 1000.

In a nineteenth embodiment of the invention, it is provided that the medium is compressible, having, especially, a compressibility $K=-1/V \cdot dV/dp$, which is greater than $10^{-6}$ bar$^{-1}$, and/or is at least partially gaseous. The medium can, in such case, be a gas loaded with solid particles and/or with droplets.

In a twentieth embodiment of the invention, it is provided that the medium has two or more phases. One phase of the medium can, in such case, be liquid and/or the medium can be a liquid containing gas and/or solid particles.

In a twenty-first embodiment of the invention, it is provided that the measuring system further includes a display element communicating, at least at times, with the measuring electronics, for visual signalizing at least of the density measured-value.

In a twenty-second embodiment of the invention, it is provided that the process line is embodied, at least sectionally, especially in the region at least of the density measuring point and/or in the region at least of the pressure measuring point, as a pipeline essentially stable in form at least under operating pressure, especially in the form of a rigid pipeline and/or a pipeline having a circular cross section.

In a twenty-third embodiment of the invention, it is provided that the process line is embodied at least sectionally, especially in the region between density measuring point and pressure measuring point and/or between density measuring point and temperature measuring point, as an essentially straight pipeline, especially a pipeline having a circular cross section.

In a twenty-fourth embodiment of the invention, it is provided that the process line has at the virtual density measuring point a caliber differing from a caliber of the process line at the pressure measuring point. Developing this embodiment of the invention further, it is provided that the caliber of the process line is greater at the pressure measuring point than the caliber of the process line at the virtual density measuring point, especially it is provided that a caliber ratio of the caliber of the process line at the pressure measuring point to the caliber of the process line at the virtual density measuring point is kept greater than 1.1.

In a twenty-fifth embodiment of the invention, it is provided that a caliber ratio of a caliber of the process line at the pressure measuring point to a caliber of the process line at the virtual density measuring point is kept smaller than 5.

In a twenty-sixth embodiment of the invention, it is provided that a caliber ratio of a caliber of the process line at the pressure measuring point to a caliber of the process line at the virtual density measuring point is kept in a range between 1.2 and 3.1.

In a twenty-seventh embodiment of the invention, it is provided that the process line has, between the virtual density measuring point and the pressure measuring point, a line segment which is embodied as a diffuser, especially a funnel-shaped diffuser, having a lumen widening in the flow direction, especially continuously widening.

In a twenty-eighth embodiment of the invention, it is provided that the process line has, between the virtual density measuring point and the pressure measuring point, a line segment which is embodied as a nozzle, especially a funnel-shaped nozzle, having a lumen narrowing in the flow direction, especially continuously narrowing.

In a twenty-ninth embodiment of the invention, it is provided that the process line has at the virtual density measuring point a caliber which is essentially equal to a caliber of the process line at the pressure measuring point.

In a thirtieth embodiment of the invention, it is provided that the process line has, at the virtual density measuring point, a caliber differing from a caliber of the process line at the temperature measuring point. Developing this embodiment of the invention further, it is additionally provided that the caliber of the process line is greater at the temperature measuring point than the caliber at the virtual density measuring point, especially that a caliber ratio of the caliber of the process line at the temperature measuring point to the caliber of the process line at the virtual density measuring point is kept greater than 1.1.

In a thirty-first embodiment of the invention, it is provided that a caliber ratio of the caliber of the process line at the temperature measuring point to the caliber of the process line at the virtual density measuring point is kept smaller than 5.

In a thirty-second embodiment of the invention, it is provided that a caliber ratio of the caliber of the process line at the temperature measuring point to the caliber of the process line at the virtual density measuring point is kept in a range between 1.2 and 3.1.

In a thirty-third embodiment of the invention, it is provided that the process line has, between the virtual density measuring point and the temperature measuring point, a line segment embodied as a diffuser, especially a funnel-shaped diffuser, having a lumen widening in the flow direction, especially continuously widening.

In a thirty-fourth embodiment of the invention, it is provided that the process line has, between the virtual density measuring point and the temperature measuring point, a line segment embodied as a nozzle, especially a funnel-shaped nozzle, having a lumen becoming narrower in the flow direction, especially continuously narrower.

In a thirty-fifth embodiment of the invention, it is provided that the process line has, at the virtual density measuring point, a caliber essentially equal to a caliber of the process line at the temperature measuring point.

In a thirty-sixth embodiment of the invention, it is provided that the virtual density measuring point is placed upstream of the temperature measuring point and/or upstream of the pressure measuring point.

In a thirty-seventh embodiment of the invention, it is provided that the pressure measuring point is arranged downstream from the temperature measuring point.

In a thirty-eighth embodiment of the invention, it is provided that a separation of the pressure measuring point from the virtual density measuring point is different from a separation of the temperature measuring point from the virtual density measuring point.

In a thirty-ninth embodiment of the invention, it is provided that a separation of the pressure measuring point from the virtual density measuring point is greater than a separation of the temperature measuring point from the virtual density measuring point.

In a fortieth embodiment of the invention, it is provided that a separation of the pressure measuring point from the virtual density measuring point is greater than a caliber of the process line at the pressure measuring point and/or wherein a separation of the pressure measuring point from the temperature measuring point is greater than a caliber of the process line at the pressure measuring point.

Developing this embodiment of the invention further, it is additionally provided that a separation of the pressure measuring point from the virtual density measuring point corresponds at least to 3-times, especially more than 5-times, a caliber of the process line at the pressure measuring point and/or that a separation of the pressure measuring point from the temperature measuring point corresponds at least to 3-times, especially more than 5-times, a caliber of the process line at the pressure measuring point.

In a forty-first embodiment of the invention, it is provided that the measuring electronics includes a microcomputer. Developing this embodiment of the invention further, it is additionally provided that the measuring electronics produces at least the density measured-value by means of the microcomputer.

In a forty-second embodiment of the invention, it is provided that the measuring system further includes at least one electronics housing, especially an explosion- and/or pressure- and/or impact- and/or weather-resistant housing, in which the measuring electronics is at least partially accommodated. In a further development of this embodiment, it is additionally provided that the at least one, especially metal, electronics housing is held to the process line and/or placed in the immediate vicinity of the virtual density measuring point.

A basic idea of the invention is to improve accuracy of measurement of measuring systems of the described kind by ascertaining, with improved accuracy, the density derived from, indeed, real, but, however, of necessity, distributedly measured, state variables. This derived density serves as a central measured variable in numerous applications of industrial measurements technology in the case of flowing media. The improved accuracy is achieved by taking into consideration possible spatial variance, especially also the degree thereof, of Reynolds number and/or thermodynamic state of the flowing medium. This is done in the case of the measuring system of the invention by a reliable calculating of the density, by referencing it to a reference point defined earlier for the particular measuring system and serving as a locationally fixed, imaginary, measuring point. The density is, thus, measured virtually. Developing this basic idea further, the measurement accuracy, with which the measuring system ascertains the local density, can be significantly improved further by having the measuring system ascertain said density also taking into consideration an equally locally measured, extant flow velocity, in order to achieve a further compensation of the error accompanying the mentioned variances of Reynolds number and/or thermodynamic state of the flowing medium.

The invention is based, in such case, on the surprising discovery that spatial variance in the Reynolds number and/or in the thermodynamic state, and the measurement errors associated therewith, can be projected onto a single dimension lying in the flow direction and/or coinciding with the flow axis of the measuring system and, thus, can be mapped into a correspondingly simplified set of measuring system parameters, which can be ascertained, at least predominantly in advance, experimentally and/or with computer support, for example in the course of a calibration of the measuring system, during completion of manufacturing and/or during start-up of the same. The spatial variances, or their extent and, as a result, also the set of device parameters, are, it is true, specific for each concrete measuring system and each concrete medium, so that the calibration is individual, but such can then, however, be viewed as invariant in the face of possible changes of Reynolds number and/or thermodynamic state arising during operation, if the measuring system remains unchanged, with essentially constant medium as regards its chemical composition. In other words, for a given, distributed measuring system, the size of changes of the thermodynamic state arising along the flow axis can be determined ahead of time, so that their influence can be calibrated and, as a result, also compensated with accuracy sufficient for the measurements, with it having been found, surprisingly, that the size of the change is largely constant for a given measuring system with constant medium, so that such can be mapped into a set of, it is true, specific, but also constant, device parameters.

An advantage of the invention is additionally to be seen in the fact that the fundamental method can be directly retrofitted into numerous, already installed, measuring systems, at least insofar as the measuring device electronics permits a change of the pertinent processing software.

BRIEF DESCRIPTION OF THE DRAWINGS

The invention, as well as additional advantageous embodiments, will now be explained in the following on the basis of examples of embodiments, on occasion with reference to the drawing, the figures of which show as follows.

DETAILED DISCUSSION

Figure 1:
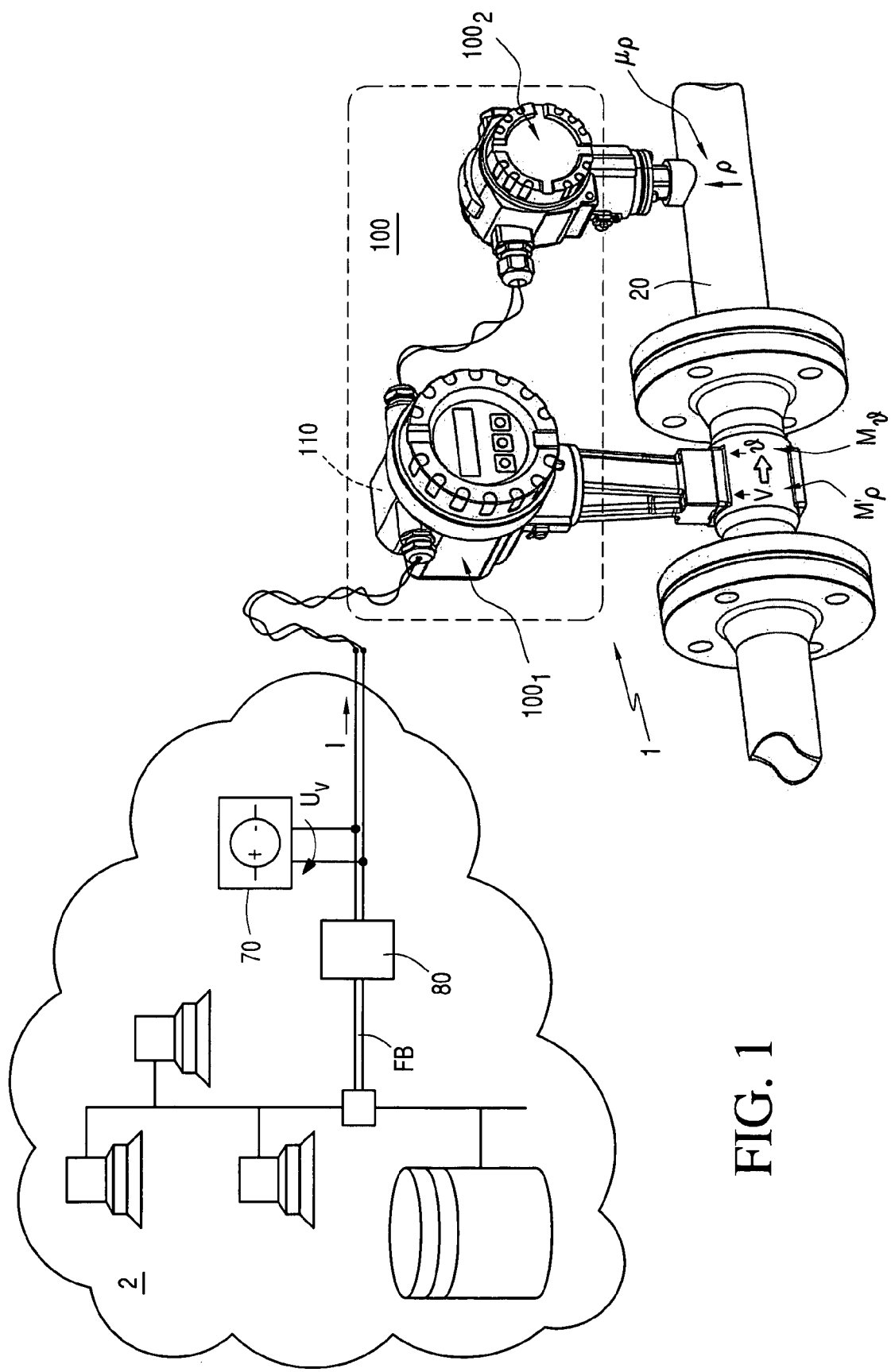
FIG. 1 perspectively, in side view, a measuring system for measuring a local density possessed by a medium flowing in a process line at a density measuring point, by means of a pressure sensor arranged at a pressure measuring point and a temperature sensor arranged at a temperature measuring point.

FIG. 1 shows, schematically, a measuring system 1, which can be modularly constructed and which is suitable, and provided, for ascertaining, at least at times, and very precisely, and, equally very robustly, a density of a medium flowing in a process line 20 and for mapping such, occasionally even in real time, into a corresponding, reliable, for example even digital, density measured-value $X_\rho$. Besides a single phase medium, it is also possible that the medium can have two or more phases. Examples of media include e.g. gas, liquid (which can contain gas and/or solid particles), a gas containing solid particles and/or droplets, vapor or steam (which can be a saturated vapor or dry steam), or the like, such as hydrogen, nitrogen, chlorine, oxygen, helium or compounds and/or mixtures formed thereof, such as e.g. carbon dioxide, water, phosgene, air, natural gas or other hydrocarbon mixtures.

Especially, the measuring system serves for measuring, very accurately, the density of the flowing medium also for the case in which the medium is variable as regards a thermodynamic state in the direction along the flow axis of the measuring system, such as can be the case, for example, in situations involving media reacting within the process line or for sectionally cooled media or for sectionally heated media, compressible media and/or in the case of process lines of cross section varying in the direction of the flow axis. The measuring system is further provided for ascertaining density of flowing media having a Reynolds number, Re, greater than 1000, and/or compressible media having a compressibility, K, of more than $10^{-6}$ $bar^{-1}$.

The measuring system includes therefor: At least one temperature sensor placed at a temperature measuring point $M_\Theta$, primarily reacting to a local temperature, $\Theta$, and delivering at least one temperature measurement signal $x_\Theta$ influenced by such local temperature, of the medium to be measured flowing past; as well as at least one pressure sensor placed at a pressure measuring point $M_p$, reacting primarily to a local, e.g. static and/or absolute, pressure, p, of, and delivering at least one pressure measurement signal $x_p$ influenced by such local pressure in, the medium to be measured flowing past. Although the pressure measuring point in the example of an embodiment shown here is located downstream from the temperature measuring point, it can, in case required, of course, also be arranged upstream of the temperature measuring point.

Besides the temperature sensor and pressure sensor, the measuring system includes, additionally, at least one measuring electronics 100 communicating, at least at times, both with the temperature sensor and with the pressure sensor and receiving, by wire and or wirelessly, measurement signals $x_\Theta$, $x_p$ from the temperature sensor and the pressure sensor. The measurement signals $x_\Theta$, $x_p$ can, if required, be appropriately converted before being sent to the measuring electronics 100.

Serving as temperature sensor can be, for example, an industrial temperature sensor such as e.g. a thermocouple or a resistance thermometer of type Pt 100 or Pt 1000, while the pressure sensor can be, for example, an industrial, especially absolutely, and/or relatively, measuring, pressure sensor, e.g. one with a capacitive pressure measuring cell. Of course, if necessary, also other pressure measuring cells converting pressures registered and transferred from the medium into corresponding measurement signals can be used, as well as other suitable temperature sensors. The temperature sensor can, additionally, be provided, for example, as a component of a self-sufficient, industrial grade, temperature measuring device having its own measuring-device electronics. Such temperature measuring devices, known per se to those skilled in the art, are well established in industrial process measurements technology and are sold, for example, also by the firm, Endress+Hauser Wetzer GmbH+Co. KG, under the designations "Easytemp TSM" or "Omnigrad T". Alternatively thereto or in supplementation thereof, the temperature sensor can, as explained in more detail below, also be embodied as an integral part of a complex in-line measuring device possibly registering even a plurality of measurement variables of the flowing medium. Equally, the pressure sensor also can be an integral part of such a complex, inline, measuring device, or a component of a self-sufficient, industrial grade, pressure measuring device with its own measuring-device electronics. Such pressure measuring devices, likewise known to those skilled in the art, are also well established in industrial process measurements technology and are sold, for example, also by the firm, Endress+Hauser GmbH+Co. KG under the designations "Cerabar S", "Cerabar M" or "Cerabar T". Also, the pressure sensor and the temperature sensor can, however, also be provided in the form of a single measuring device for pressure and temperature measurement, for example, an industrial, combination, measuring device as proposed in WO-A 97/48970.

As shown schematically in FIG. 1, the measuring electronics can be accommodated, at least partly, in an electronics housing 110, especially an explosion- and/or pressure- and/or impact- and/or weather-resistant housing. The electronics housing 110, for example of metal, can, as also shown in FIG. 1, on occasion, be mounted on the process line.

For the measurement-system-internal, further processing of the pressure measurement signal and the temperature measurement signal, an embodiment of the invention additionally provides in the measuring electronics a microcomputer μC, which serves especially also for producing the density measured-value $X_\rho$, and which can be formed, for example, by means of at least one microprocessor and/or by means of at least one signal processor. Alternatively thereto or in supplementation thereof, for implementing the microcomputer μC, also application-specific, integrated, ASIC circuits and/or programmable logic components or systems can be used, such as e.g. so-called FPGAs (field programmable gate array) and/or, as also proposed in WO-A 03/098154, so-called SOPCs (system on programmable chip) can be used. Furthermore, the measuring electronics includes, in another embodiment of the invention, at least one display element HMI, for example, placed in the immediate vicinity of the measuring electronics and communicating, at least at times, with the measuring electronics, especially with the microcomputer possibly provided therein, for the visual signaling at least of the density measured-value. Display element HMI can, in such case, be embodied also in the form of a combined, display and servicing element, which permits, besides the visualizing of measured-values, also user input of service commands parametering, and/or controlling, the measuring electronics.

In a further embodiment of the invention, it is additionally provided that the measuring electronics generates, based on the temperature measurement signal, for example also with application of the, on occasion, provided microcomputer, repetitively, a temperature measured-value $X_\Theta$, especially a digital one, instantaneously representing a local temperature of the medium, especially the temperature of the medium at the temperature measuring point, and/or that the measuring electronics generates, based on the pressure measurement signal $x_p$, for example, in turn, with application of the, on occasion, provided microcomputer, repetitively, a pressure measured-value $X_p$, especially a digital one, instantaneously representing a pressure reigning in the medium, especially at the pressure measuring point.

At least for the above-described case, in which the measuring system is formed by means of two, or also more, self-sufficient, measuring devices, in the case of the measuring system of the invention, also the measuring electronics itself can be implemented by appropriate interconnecting, by wire and/or wirelessly, of individual measuring device electronics thus forming subcomponents of the measuring electronics and can, as a result, also be built-up modularly. In such case, the measuring electronics can communicate with the temperature sensor and/or with the pressure sensor, for example, by means of a fieldbus, especially a serial fieldbus. Alternatively to a distributed construction, the measuring electronics can, however, also be embodied, in case necessary, in the form of a single electronics module, into which the measurement signals produced by the pressure and/or temperature sensors are directly fed.

The, on occasion, at least two measuring device electronics, or electronics subcomponents, $100_1$, $100_2$ are to be so coupled together in manner known to those skilled in the art that, during operation of at least one of the two measuring device electronics $100_1$, $100_2$, correspondingly produced measurement data can be transmitted at least unidirectionally to the other, functioning, thus, as master electronics. This can be done, in manner known to those skilled in the art, in the form of measurement signals coded in their voltage, their current and/or their frequency and/or in the form of measured-values encapsulated in the form of digitally coded telegrams, e.g. in the HART®-MULTIDROP method or in the burst-mode method. Of course, instead of this, however, also data connections communicating bidirectionally between the two measuring device electronics $100_1$, $100_2$ can be used for transmission of the locally ascertained, measured variables to, in each case, the other measuring device electronics $100_1$, $100_2$, respectively, for example via external fieldbus. For implementing the necessary communication connection between the two measuring device electronics $100_1$, $100_2$, it is possible to apply, in advantageous manner, standard interfaces correspondingly established in industrial measurements and automation technology, such as e.g. line-conveyed, 4-20 mA, current loops, on occasion also in connection with HART® or other applicable fieldbus protocols and/or suitable radio connections.

In a further advantageous embodiment of the invention, the at least one measuring electronics $100_1$, $100_2$ is additionally so designed, that it communicates, at least at times, as indicated schematically in FIG. 1, with a data processing system superordinated thereto, and, indeed, in a manner such that, at least in normal measuring operation, measured-values repetitively ascertained on the part of the measuring system are transferred, on occasion even in the form of a digitally coded, telegram, as near-time as possible and/or in real time, to the data processing system. For registering measured-values transmitted from the measuring electronics, data processing system 2 is additionally provided with at least one evaluating circuit 80 suitably communicating, at least at times, therewith. The superordinated data processing system 2 can be, for example, part of a process-near, automatic control unit or also a long-distance process control system having a plurality of process control computers and/or digital programmable logic controllers, which are arranged spatially distributed within an industrial plant and coupled together via a corresponding data transmission network, especially also by means of digital fieldbusses. Equally, the data processing system can be connected with further measuring devices and/or with control devices, such as e.g. valves or pumps, involved in the process. In a further development of the invention, the data processing system further includes at least one fieldbus FB, especially a serial fieldbus, serving for the transmission of digital measurement- and/or operational-data. The at least one fieldbus FB can be, for example, one operating according to one of the standards established in industrial process automation, such as e.g. FOUNDATION FIELDBUS, PROFIBUS, CANBUS, MODBUS, RACKBUS-RS 485 or the like. In an advantageous further development, it is, in such case, additionally provided that the aforementioned evaluation circuit 80 is coupled to the at least one fieldbus, especially for forwarding of measured-values received in the form of digital measurement data from the measuring system. Depending on how fieldbus and measuring electronics are embodied, the latter can be connected to the data processing system 2 either directly or by means of an adapter, which suitably converts the signal carrying the measured-value.

The measuring electronics and the data processing system 2 distanced, on occasion considerably, spatially therefrom are, in a further development of the invention, connected electrically together by means of at least one line-pair 2L, through which current I, especially a variable current I, flows, at least at times, during operation. The current can be fed, for example, from an external electrical energy, or power, supply 70 provided in the superordinated data processing system. During operation, supply 70 provides at least one supply voltage $U_v$, especially a uni-polar supply voltage, driving a current I flowing in the line-pair 2L. The energy source can, in such case, be e.g. a battery and/or a direct or alternating voltage source circuit fed via a plant-internal supply grid. For connecting, especially releasably connecting, of the at least one line-pair 2L to the measuring electronics 100 and, thus, the measuring system 1 itself, such further includes at least one, externally accessible, terminal pair.

For the above-described case of the measuring electronics assembled modularly of separate subcomponents, each of the subcomponents $100_1$, $100_2$ can, for example, be connected separately to the external energy supply, for example also by means of the aforementioned 4-20 mA current loop. Alternatively thereto or in supplementation thereof, however, also one of the subcomponents $100_1$, $100_2$ can be so connected to the other that it can feed such, at least at times, with electrical energy.

The measuring electronics is, in a further embodiment, additionally so embodied that the measured-values generated internally in the measuring system, be it, now, measured-values of a single, registered, measured variable or measured-values of diverse, registered, measured variables, such as e.g. the ascertained density and an ascertained mass flow, are transmitted at least in part, via the at least one line-pair 2L to the superordinated data processing system 2. The pair of electrical lines 2L can, in such case, be part of a so-called two-conductor current loop well proven in industrial measurements technology. For this case, then, on the one hand, the measured-values, produced at least at times, are transmitted via this single line-pair 2L to the superordinated data processing system in the form of a load modulated (for example, by means of conventional coupling circuits) loop current, especially a clocked or continuously variable, loop current, and, on the other hand, the measuring electronics, and, thus, the measuring system, are supplied, by means of a corresponding, especially clocked, DC inverter, at least at times and/or at least in part, with electrical energy, or electrical power $I_N \cdot U_N$, via the line pair 2L.

The measuring electronics 100 is, in a further embodiment of the invention, additionally designed for generating, during operation, a plurality of measured-values, especially digital measured-values, representing, at least in part, the at least one measured variable and for transmitting such, at least partially, via terminals and the line pair 2L appropriately connected thereto, to the connected data processing system 2 in a form appropriate for the data processing system 2. In case required, the measuring system can, in this connection, be further developed such that the measuring electronics 100 and data processing system 2 are also connected together by means of at least one additional, second line pair (not shown), through which, during operation, at least at times, an electrical current correspondingly flows. For this case, the measuring system can further transmit the internally generated measured-values, at least partially also via the additional line-pair to the data processing system. Alternatively thereto or in supplementation thereof, measuring system and data processing system can also communicate with one another wirelessly, for example by means of radio waves. Especially for this last case, it can also be of advantage to supply the measuring system with electrical energy, especially also exclusively, by means of an internal and/or external, especially replaceable and/or re-chargeable, battery and/or fuel cell. Moreover, the measuring system can additionally be fed, partially or exclusively, by means of power converters using regenerative energy sources and placed directly on the field measuring device and/or placed remotely therefrom, examples of such power converters being e.g. thermogenerators, solar cells, wind generators, and the like.

In a further embodiment of the invention, it is provided that the measuring system can exchange via the measuring electronics, at least at times, with an external service- and control-unit, for example a handheld service unit, or a programming device provided in the superordinated data processing system, device-specific data, such as settings-parameters, internal to the measuring device, for the measuring electronics itself and/or diagnostic parameters internal to the measuring system. For this purpose, provided in the measuring electronics 100 is, additionally, at least one communication circuit COM, which controls communications on the at least one line pair 2L. Especially, the communication circuit serves for converting the measuring-system-specific data to be sent, into signals transmittable via the pair 2L of electrical lines and to then couple such signals into the lines. Alternatively thereto or in supplementation thereof, the communication circuit COM can, however, also be designed for receiving measuring system specific data, for example a set of settings-parameters to be changed for the measuring electronics, sent from the exterior via the pertinent pair of electrical lines. The communication circuit can be e.g. an interface circuit working according to the HART@-Field-Communications-Protocol (HART Communication Foundation, Austin, Tex.), which applies high frequency, FSK-coded (frequency shift keying), alternating voltages as signal carrier, or, however, also one working according to the PROFIBUS standard. In case required, also, additionally, externally running (for example in a runtime environment of the superordinated data processing system) processes communicating with the measuring electronics 100 and processing data can have direct access to the measuring electronics.

In the case of the measuring system of the invention, it is further provided that the measuring electronics produces during operation, with application at least of the temperature measurement signal $x_\Theta$ as well as the pressure measurement signal $x_p$, the density measured-value $X_\rho$ in such a manner that it represents an instant, local density, which the flowing medium actually has at an imagined reference point (which can also be predeterminably spaced from the real pressure measuring point and/or the real temperature measuring point along the flow axis) defined locally within the process line 20. This imagined reference point, in the absence of a corresponding density sensor thereat and for distinguishing from the actually formed and, thus, real measuring points provided by means of the temperature sensor and pressure sensor, respectively, is referred to as a virtual density measuring point M'$_\rho$. The virtual density measuring point M'$_\rho$ can, in such case, both be referenced to a reference point selected during operation from a plurality of predetermined reference points and, thus, be locationally variable in defined manner and it can also be kept locationally fixed. At least for the last case, a further embodiment of the invention provides that the electronics housing, with the measuring electronics located therein, is placed in the immediate vicinity of the virtual density measuring point M'$_\rho$. The definition of the virtual density measuring point M'$_\rho$ occurs, in such case, by a corresponding configuration of the measuring electronics, especially the calculative method executed therein for purposes of the density measurement, taking into consideration position and geometric character of the real measuring points M$_p$, M$_\Theta$. In such case, according to a further embodiment of the invention, it is provided that the virtual density measuring point M'$_\rho$ is situated upstream of the temperature measuring point M$_\Theta$ and/or upstream of the pressure measuring point M$_p$. Furthermore, it can be of advantage for ascertaining the density, to permit the density measuring point to coincide either with the temperature measuring point or with the pressure measuring point.

In the case of the measuring system being discussed, it is presumed, in such case, that the flowing medium has at least one state variable, for example a temperature and/or a pressure and/or a density, and/or a Reynolds number Re, which, singly or together, assume(s), at the virtual density measurement point M'$_\rho$, at least at times, especially in the time period relevant for production of the density measured-value and/or repetitively, an, at least in the sense of a measurement accuracy desired for the density measurement, significantly different magnitude than at least one of the real measuring points delivering actual measurement signals, thus, the temperature measuring point and/or the pressure measuring point. In other words, one proceeds with the understanding that the medium at the virtual density measuring point is, at least at times, in a thermodynamic state and/or in a flow state, which differ(s) significantly, especially to a degree significant for a desired measuring accuracy of the measuring system, as regards at least one, local, thermodynamic state variable (temperature, pressure, density, etc.) from a thermodynamic state of the medium at the temperature measuring point and/or from a thermodynamic state of the medium at the pressure measuring point. This spatial variance of thermodynamic state and/or flow state in the flowing medium can arise, as already mentioned, e.g. in the case of a compressible medium, a medium reacting in the process line, an additionally cooled medium or an additionally heated medium. Moreover, such a variance of thermodynamic state and/or flow state can also be brought about by allowing the medium to flow through a process line which is sectionally narrowing and/or sectionally widening along the flow axis, such as is the case, for example, in the application of nozzles or diffusers in the process line, so that the medium is accelerated or decelerated, on occasion accompanied by a compression or an expansion of the same.

In an embodiment of the invention, it is, therefore, additionally provided that the measuring electronics, based on the pressure measurement signal as well as the temperature measurement signal, ascertains first a provisional density measured-value X'$_\rho$, for example according to one of the mentioned industrial standards AGA 8, AGA NX-19, SGERG-88 IAWPS-IF97, ISO 12213:2006, for representing a density which the flowing medium solely apparently has at the virtual density measurement point, this because of preliminarily neglecting the spatial variances being discussed as regards the thermodynamic state and/or the flow state.

The ascertaining of the provisional density measured-value X'$_\rho$ can, in such case, be accomplished, at least at times, especially also for at least partially gaseous media, such as natural gas, air, methane, phosgene, etc., based on the formula:

$$X'_\rho = \frac{n}{z \cdot R_M} \cdot \frac{X_p}{X_\vartheta} \tag{1}$$

wherein n is a molar mass, z a real gas factor of the medium ascertained according to one of the industry standards AGA 8, AGA NX-19, SGERG-88 IAWPS-IF97, ISO 12213:2006 and/or with application of the temperature measurement signal and/or the pressure measurement signal, and R$_M$ the relative gas constant of the medium, corresponding to the absolute gas constant R normalized with the molar mass n of the medium, thus R/n, with R=8.3143 J/(K mol).

Alternatively thereto or in supplementation thereof, the measuring electronics can ascertain the provisional density measured-value X'$_\rho$, at least at times, especially in the case of media containing, at least in part, steam, based on the formula:

$$X'_\rho = \pi_{IAWPS\text{-}IF97} \cdot \gamma_{IAWPS\text{-}IF97} = \frac{X_p}{P^*_{IAWPS\text{-}IF97}} \cdot \frac{g_{IAWPS\text{-}IF97}}{R_M \cdot X_\vartheta} \tag{2}$$

wherein $\pi_{IAWPS\text{-}IF97} = X_p/P^*_{IAWPS\text{-}IF97}$ and $\gamma_{IAWPS\text{-}IF97} = g_{IAWPS\text{-}IF97}/(R_M^* X_\Theta)$, with P* being a medium-specific, critical pressure according to the industrial standard IAWPS-IF97, especially 16.53 MPa, for the case in which the medium to be measured is water, above which the medium to be measured cannot be liquid, and $g_{IAWPS\text{-}IF97}$ a medium-specific, free enthalpy (Gibbs free energy) according to the industrial standard IAWPS-IF97.

Selection of the currently actually suitable, calculative formula for the provisional density measured-value X'$_\rho$ and, thus, in the end, also for the actual density measured-value X$_\rho$ can, in such case, be accomplished automatically and/or in dialog with the user on-site, or, via a superordinated data processing system, semi-automatically, on occasion also taking into consideration the currently measured pressure and the currently measured temperature and/or according to the selection method proposed in the initially mentioned WO-A 2004/023081.

In a further embodiment of the invention, it is additionally provided that the measuring electronics produces the density measured-value also with application of at least one numerical compensation factor K, for example a digitally stored compensation factor, corresponding with a measuring-system-specific and medium-specific, locational variability arising along the flow axis of the medium for at least one thermodynamic state variable of the medium, especially temperature, pressure or density itself, and/or corresponding with a measuring-system-specific and medium-specific, locational variability arising along the flow axis of the medium for the Reynolds number of the flowing medium.

The aforementioned locational variabilities and, as a result, the compensation factor K can, in such case, be determined in advance, at least for measuring systems with conditions remaining constant, and/or, during operation, for example taking into consideration the medium actually to be measured, especially its chemical composition and/or its thermodynamic properties. The ascertaining of the compensation factor K can occur e.g. during a calibration of the measuring system with known reference medium and/or during start-up of the measuring system on-site. For certain applications, especially with media of chemical composition which remains constant and thermodynamic properties which remain constant, it can be quite sufficient to ascertain the at least one compensation factor K at least once, solely during start-up of the measuring system. In the case of media changing significantly during operation of the measuring system as regards composition and/or thermodynamic properties, on occasion also as a result of replacement of the same, it can, however, be quite advantageous to have the measuring electronics ascertain the compensation factor K repetitively also following the start-up, during operation of the measuring system. The ascertaining of the compensation factor K can, in such case, be carried out on the basis of a predetermined (on occasion ascertained in dialogue with the user, on-site or remotely, and/or externally of the measuring electronics) specific heat capacity, $c_p$, of the current medium. For example, the heat capacity, $c_p$, or also other parameters for specifying the medium currently to be measured, can be transmitted from the superordinated data processing system to the measuring electronics and thus, as well, to the measuring system.

In another further development of the invention, the measuring electronics includes, especially for simplifying the ascertaining of the compensation factor K, at least one data memory 16, especially a non-volatile data memory, for storing measurement system parameters required for operating the measuring system, especially for defining its measuring and transmitting functionalities. Especially, it is, in such case, further provided that the data memory, for example a data memory in the form of a table memory and/or a non-volatile memory, stores, at least at times, the at least one compensation factor K, if necessary, also when the measuring electronics is turned off. For example, the data memory can store for such purpose also a plurality of compensation factors ascertained for a different media and/or for different circumstances of installation, so that the measuring electronics can select from a plurality of compensation factors stored in the data memory the at least one currently appropriate compensation factor K, taking into consideration the current medium as well as the current circumstances of installation.

Especially also for ascertaining the compensation factor K, a further embodiment of the invention additionally provides that the data memory stores, at least at times, at least one measuring system parameter $SP_M$ of a first kind solely specifying the medium currently to be measured and that the measuring electronics ascertains the density measured-value $X_\rho$ with application at least of the at least one measuring system parameter $SP_M$ of the first kind. The measuring system parameter $SP_M$ of the first kind can be, for example, a specific heat capacity, $c_p$, of the medium currently to be measured, a molar mass, n, of the medium and/or the number, f, of oscillatory degrees of freedom of the atoms or molecules of the medium, as determined by the molecular structure of the medium, and/or parameters derived therefrom, such as e.g. the real gas or also (super-) compressibility factor, on occasion also ascertained according to one of the industrial standards AGA 8, AGA NX-19, SGERG-88 IAWPS-IF97, ISO 12213:2006. As a result, it is clear that, accordingly, also two or more of such measuring system parameters $SP_M$ of the first kind, of different dimensions and/or units of measurement, can be stored in the data memory for specifying the medium currently to be measured.

In a further embodiment of the invention it is additionally provided that the data memory stores, at least at times, at least one measuring system parameter $SP_{ME}$ of the second kind specifying both the medium currently to be measured as well as also instantaneous circumstances of installation of the measuring system, and that the measuring electronics ascertains the density measured-value $X_\rho$ with application at least of the measuring system parameter $SP_{ME}$ of the second kind and, especially, however, also with application of the measuring system parameter $SP_M$ of the first kind. The circumstances of installation are, in such case, determined, at least to a degree significant for the ascertaining of the density measured-value, by the arrangement of pressure-, temperature- and/or density measuring point(s) relative to one another, as well as, in each case, by the form and size of the process line in the region of the pressure-, density- and/or temperature measuring point(s). Consequently, the measuring system parameter $SP_{ME}$ of the second kind can be, for example, a part of a parameter set reflecting the measuring points as regards their actual positions and actual character of the process line in the region of the measuring points, as well as also the thermodynamic properties of the medium currently to be measured, or also can be a numerical value of a complex parameter appropriately taking into consideration such influences, definitively ascertained, for example experimentally and/or empirically, first during operation of the measuring system, on occasion also with application of the measuring system parameter $SP_M$ of the first kind.

In a further embodiment of the invention, it is additionally provided that the measuring electronics receives, at least at times, especially telegraphed from the superordinated data processing system and/or ascertained in near-time, numerical parameter values for at least one medium to be measured and/or measuring system parameters $SP_M$, $SP_{ME}$ specifying instantaneous circumstances of installation of the measuring system, for example, thus, the heat capacity, $c_p$, for medium to be measured currently and/or in the future. The heat capacity, $c_p$, or also an equally transmitted, other system parameter $S_M$ of the first kind can, in such case, be ascertained in advance by a corresponding measurement performed, for example, by the density measuring point and/or also externally of the measuring system and/or by an input from the user-side, on occasion also with application of the superordinated data processing system. Further, it is, therefore, also provided in the measuring system of the invention that the measuring electronics communicating, at least at times, by line or by radio, with the superordinated, electronic, data processing system transmits the density measured-value to the data processing system and/or that the measuring electronics, at least at times, receives, from the data processing system, numerical parameter values, especially in the form of a standardized telegram, for the medium currently to be measured, for example, thus, measuring system parameters $SP_M$ of the first kind specifying its thermodynamic properties and/or its chemical composition. If required, it is also additionally possible to ascertain, by means of the data processing system, measuring system parameters $SP_{ME}$ of the second kind and to transmit such in the form of numerical parameter values directly to the measuring electronics.

For the described case, in which the measuring electronics is to automatically ascertain during operation, on the basis of system parameters $S_M$ of the first kind, at least at times, the specific heat capacity, $c_p$, of the medium currently to be measured, such can be done, for example, based on the formula:

$$c_P = \left(1 + \frac{f}{2}\right) \cdot \frac{R}{n}, \tag{3}$$

wherein n is the measuring system parameter, molar mass, R, the absolute gas constant, with R=8.3143 J/(K·mol), and f, the measuring system parameter, number of oscillatory degrees of freedom of the atoms or molecules of the medium currently to be measured.

In a further embodiment of the invention, it is provided that the compensation factor is determined solely by the medium currently to be measured, especially its chemical composition, as well as the physical properties derived directly therefrom, as well as the concrete embodiment of the measuring system as regards installation sizes and installed positions of the individual measuring points, as well as size and form of the process line in the region of the measuring points, so that it, in the end, is largely independent of the really measured, measurement variables, pressure and temperature.

On account of, and considering, the fact that the variance of the thermodynamic state, or the flow state, of the flowing medium and, in accompaniment therewith, the measurement accuracy of such measuring systems can be quite co-determined also by the actual flow velocity of the medium, a further embodiment of the invention additionally provides that the measuring electronics ascertains the density measured-value $X_\rho$ with application at least of a density correction value $X_K$ ascertained during run-time and depending both on a flow velocity of the medium and also on the local temperature reigning at the temperature measuring point. This density correction value $X_K$ is, in such case, so embodied that it corresponds with an instantaneous local variability at least of a thermodynamic state variable of the medium, especially such as depends on the medium currently to be measured as well as on instantaneous circumstances of installation and/or which corresponds with an instantaneous local variability of the Reynolds number of the flowing medium, especially such as results from the medium and/or the construction of the measuring system and occurs along the flow axis of the measuring system.

For this, a further embodiment of the invention provides that available, at least at times in the measuring electronics, is a corresponding velocity measured-value $X_v$ representing instantaneously, as currently as possible, a flow velocity of the medium flowing in the measuring system.

With application of the velocity measured-value $X_v$ and the temperature measured-value $X_\Theta$, as well as the already mentioned, compensation factor K, then, the density correction value $X_K$ can be very simply ascertained by means of the measuring electronics based on the formula $$X_K = \frac{1}{\left(1 + K \cdot \frac{X_v^2}{X_\vartheta}\right)}. \tag{4}$$

At least for the above-described case, in which the measuring electronics 100 ascertains the provisional density measured-value $X'_\rho$ by means of a calculative algorithm based on the calculative formula (1) and/or on the calculative formula 2, the density measured-value $X_\rho$ for the virtual measured density can be very simply and rapidly ascertained with application both of the provisional density measured-value $X'_\rho$ and also the density correction value $X_K$ additionally with the formula:

$$X_\rho = X'_\rho \cdot X_K. \tag{5}$$

Accordingly, in a further embodiment of the invention, the measuring electronics is so configured that it ascertains the density measured-value $X_\rho$ with application of the above formulas (4), (5), as well as (1) or (2), at least at times, based on the formula:

$$X_\rho = \frac{n \cdot X_p}{z \cdot R_M \cdot (X_\vartheta + K \cdot X_v^2)} = \frac{n \cdot X_p}{z \cdot R_M \cdot X_\vartheta} \cdot \frac{1}{\left(1 + K \cdot \frac{X_v^2}{X_\vartheta}\right)} \tag{6}$$

and/or, at least at times, based on the formula:

$$X_p = \pi_{IAWPS\text{-}IF97} \cdot \gamma_{IAWPS\text{-}IF97} \cdot \frac{1}{\left(1 + K \cdot \frac{X_v^2}{X_\vartheta}\right)} \tag{7}$$

$$= \frac{X_p}{P^*_{IAWPS\text{-}IF97}} \cdot \frac{g_{IAWPS\text{-}IF97}}{R_M \cdot X_\vartheta} \cdot \frac{1}{\left(1 + K \cdot \frac{X_v^2}{X_\vartheta}\right)}.$$

For testing the plausibility of the instantaneously ascertained, density measured-value, for example in the course of a self-validation of the measuring system, the measuring electronics, in a further, advantageous embodiment of the invention, compares the density correction value $X_K$ during operation repetitively with at least one reference value specific to the predetermined measuring system. Developing this further, in such case, it is provided that the measuring electronics, based on the comparison of density correction value $X_K$ and reference value, quantitatively signals an instantaneous deviation of the density correction value $X_K$ from the reference value and/or, at times, generates an alarm signaling an undesired, especially unallowably high, discrepancy between density correction value $X_K$ and associated reference value. Alternatively thereto or in supplementation thereof, the measuring electronics is additionally so embodied that it ascertains, repetitively during operation, a density error, which corresponds with a deviation, especially a relative deviation, of provisional density measured-value $X'_\rho$ and density measured-value $X_\rho$, especially such values ascertained according to standards in the above sense, and also issues such in the form of a numerical density error value. An impermissibly high discrepancy between provisional density measured-value $X'_\rho$ and density measured-value $X_\rho$, or between density correlation value $X_K$ and associated reference value, can, for example, be attributed to an erroneously parametered measuring electronics, or an unexpected change of the medium to be measured and/or a disturbance of a plant containing the process line. In view of this, in an embodiment of the invention, it is provided that the measuring electronics only applies the density correction value $X_K$ in the generating of the density measured-value $X_\rho$ when it amounts to at least one, especially lies in a range between 1 and 1.2. In an embodiment alternative thereto, the measuring electronics is so configured that it applies the density correction value $X_K$ in the generation of the density measured-value $X_\rho$ only when it amounts to, at most one, especially lying in a range between 0.8 and 1. Additionally, it can be of advantage for the user, when the measuring electronics outputs the instantaneous density error in the form of a numerical density error value and/or compares the instantaneous density error with at least one predetermined reference value and, based on this comparison, generates, at times, an alarm, which signals the undesired, especially impermissibly high, discrepancy between provisional density measured-value $X'_\rho$ and density measured-value $X_\rho$, for example, on-site, by means of the display element HMI.

In a further development of the invention, the measuring system additionally delivers at least one flow measurement signal $x_v$ influenced by the local flow velocity. This is done especially also for the purpose of automatic and near-time ascertaining of the density correction value $X_K$. In order to accomplish the delivery of this at least one flow measurement signal $x_v$, the measuring system is equipped with at least one flow sensor placed at a velocity measuring point $M_v$ for reacting primarily to a local flow velocity of the medium to be measured, especially to a flow velocity averaged over a cross section of the process line, especially also to changes of the flow velocity. During operation, measuring electronics 100 and flow sensor therefore communicate, at least at times, with one another, at least in a manner such that the measuring electronics has available to it, at least at times, the flow measurement signal $x_v$ generated by the flow sensor. Especially, it is, in such case, additionally provided that the measuring electronics ascertains the density measured-value $X_\rho$ also with application of the flow measurement signal. At least therefor, the measuring electronics communicates, at least at times, also with the flow sensor, e.g. also via external fieldbus and/or wirelessly by radio. Furthermore, it is provided that the density measured-value is generated by means of the measuring device electronics in such a manner that it represents a locational density of the medium in the region of the flow sensor.

In the example of an embodiment shown here, at least the flow sensor, especially, however, also one of the electronics modules of the measuring electronics, is provided by means of an industrial grade, in-line, measuring device for flowing media, for instance one embodied as a compact device. The in-line measuring device includes at least one, essentially rigid and sufficiently pressure resistant, carrier tube, through which the medium to be measured flows during operation, especially a carrier tube inserted into the course of the process line and, thus, forming a line-segment of the same. On and/or in the carrier tube is appropriately placed the actual flow sensor. Depending on application, the carrier tube can be made, for example, of metal, plastic and/or ceramic.

In the case of the example of an embodiment shown here by way of example, the flow sensor is provided by a compact in-line measuring device in the form of a vortex flow meter inserted into the course of the process line. Such vortex flow meters serve, conventionally, for registering, highly accurately, as primary physical, measured variable, a flow velocity and/or volume flow of flowing media, especially media of high temperature and/or high pressure.

Figure 3A:
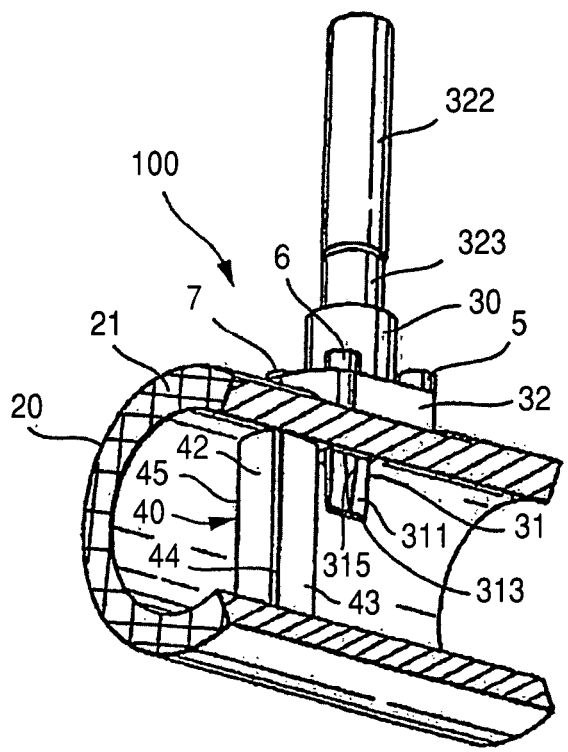
FIGS. 3a, 3b perspectively and partially sectioned, in views from different angles, eddy flow transducer suitable for application in a measuring system of FIG. 1 and working according to the vortex principle.
Figure 3B:
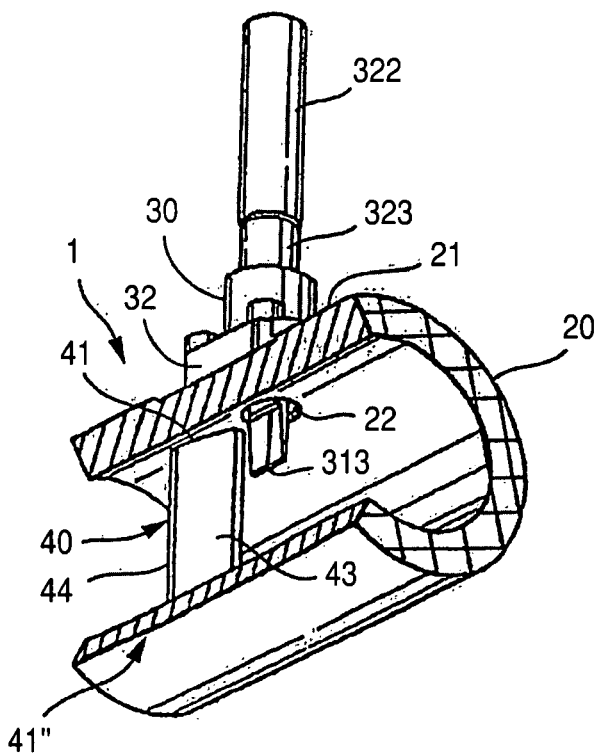

The views selected in FIGS. 3a and 3b show the vortex flow meter perspectively in section, in one case seen in the flow direction (FIG. 3a) and, in the other case, seen counter to the flow direction (FIG. 3b). The vortex flow meter includes a vortex sensor 30 fixed on a tube wall 21 of a carrier tube 20 serving as a line segment of the process line. Vortex sensor 30 extends through a bore 22 formed in tube wall 21 and serves as flow sensor in the above sense. Vortex sensor 30 can be, for example, a dynamically compensated, vortex sensor having a paddle immersed in the medium and a capacitive transducer element registering its deformations, as such is also described in U.S. Pat. No. 6,003,384.

In the interior of the carrier tube 20, which itself is inserted into the pipeline, for example, by means of appropriate flange connections, additionally arranged along one of the diameters of the carrier tube is a bluff body 40, which is securely connected with the carrier tube 20 at diametrically oppositely lying, securement locations 41, 41*. The center of the bore 22 and the center of the securement location 41 lie on a generatrix of the carrier tube 20. Bluff body 40 includes an impingement surface 42, against which medium to be measured flows during operation. Bluff body 40 has, additionally, two side surfaces, of which only a facing side surface 43 is visible in FIGS. 3a and 3b. Formed by the impingement surface 42 and the side surfaces are two separation edges, of which only a facing separation edge 44 is visible completely in both views, while the location of the rear separation edge is evident in FIG. 3a. Bluff body 40 of FIGS. 3a and 3b has, here, essentially the form of a right, triangular column, thus a perpendicular column of triangular cross section. In case required, of course, also bluff bodies of other shape can be applied for implementing the measuring system of the invention.

By the flowing of the medium against the impingement surface 42, there forms downstream of the bluff body, in known manner, a Karman vortex street, in that vortices separate alternately at each separation edge and then proceed downstream in the flowing medium. These vortices entrained by the flow produce, in turn, local pressure fluctuations in the flowing medium and their time-referenced separation frequency, thus their so-called vortex frequency, is a measure for the flow velocity and/or the volume flow of the medium. The pressure fluctuations released from the entrained vortices are then converted by means of the vortex sensor 30, formed, here, by means of paddle and placed downstream of the bluff body, into a vortex signal corresponding to the local flow velocity and serving as electrical, flow measurement signal $x_v$.

The transducer element 36 produces the above-mentioned measurement signal, whose frequency is proportional to the volume flow of the flowing medium.

The vortex sensor 30 is inserted downstream of the bluff body 40 into the bore 22 in the tube wall 21 of the carrier tube 20 and seals the bore 22 against escape of medium from the interior of the carrier tube 20 to the outer surface of the carrier tube 20, this being accomplished by a screwed engagement of the vortex sensor 30 with the wall 21. Serving for this are e.g. four screws, of which the screws 5, 6, 7 are visible in FIGS. 3a and 3b. Parts of the vortex sensor visible in FIGS. 3a and 3b are the wedge-shaped sensor vane 31 extending into the interior of the carrier tube 20 through the bore 22 of the tube wall 21 and a housing cap 32. Housing cap 32 runs out to an extension 322, with interposition of a thin-walled intermediate piece 323; compare, in this connection, also the already mentioned U.S. Pat. No. 6,003,384. Sensor vane 31 has principal surfaces, of which only the principal surface 311 is visible in FIGS. 3a and 3b. The principal surfaces are aligned with the mentioned generatrix of the carrier 20 and form a front edge 313. Sensor vane 31 can also have other spatial forms; thus, e.g., it can have two parallel principal surfaces, which form two parallel front edges. Sensor vane 31 is shorter than the diameter of the carrier tube 20; it is, furthermore, flexurally stiff and can include, for example, a blind hole, in which a transducer element can be inserted, in the form of a thermocouple or resistance thermometer serving to detect the temperature of the medium, on occasion for generating the temperature measurement signal and, thus, also for implementing the temperature measuring point itself; compare, in this connection, also the already mentioned U.S. Pat. Nos. 6,988,418 or 6,910,387. In order that the blind hole 314 has a sufficient diameter, wall portions protrude out of the principal surfaces, such a wall portion 315 being indicated in FIG. 3a. The blind hole 314 extends into the vicinity of the front edge 313 and has there a floor.

Figure 4:
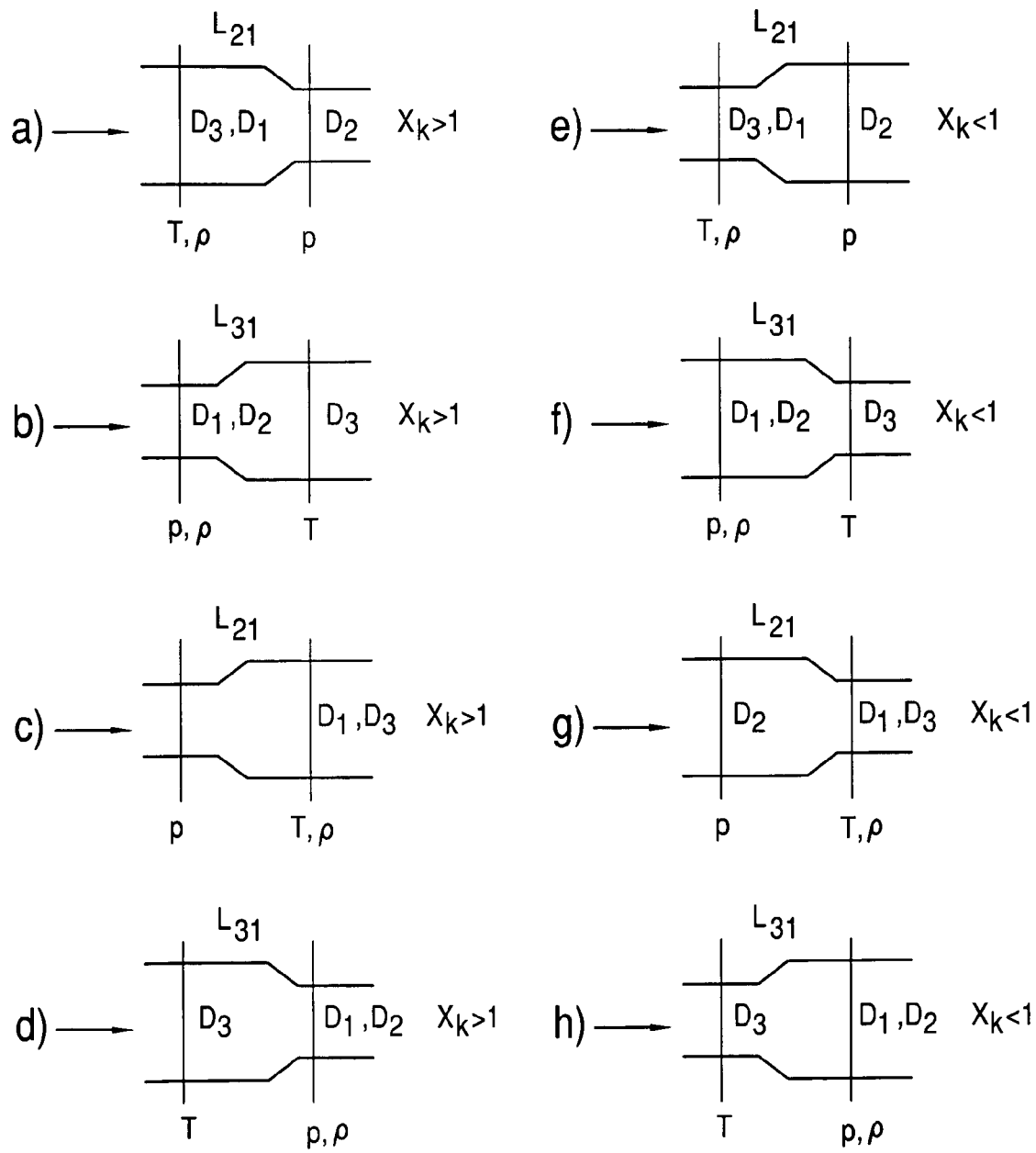
FIGS. 4a to 4h schematically in section, different variants for embodying the process line and for relative arrangement of the individual measuring points in the measuring system of FIG. 1.

To the vortex sensor 30 belongs, additionally, a diaphragm 33 covering over the bore 22 and having a first surface 331 facing the medium and a second surface 332 facing away from the medium; see FIGS. 3 and 4. Sensor vane 31 is affixed to the surface 331, while a physical-to-electrical transducer element 36 reacting to bending, or movements, of vane 31 is affixed to the surface 332. Sensor vane 31, diaphragm 33, as well as its annular edge 333, can be manufactured of a single piece of material, e.g. metal, especially stainless steel.

It is to be noted here that, instead of the vortex flow meter shown here by way of example, having at least one bluff body protruding into a lumen of the process line and immersed in the medium, and at least one flow sensor arranged downstream of the at least one bluff body, especially a flow sensor protruding at least partially into a lumen of the process line, of course, also other in-line measuring devices equally established in process automation technology can be used for providing the at least one flow sensor delivering said flow measurement signal and, thus, for forming the flow measuring point as such, examples being e.g. magneto-inductive flow meters, thermal flow meters, pressure-difference flow meters, ultrasonic flow measuring devices, or the like. The flow sensor itself can, in such case, as also usual in the case of such measuring devices, and depending on the implemented principle of measurement, be formed by means of at least one electrical resistance element, especially one through which flows, at least at times, a heating current, by means of at least one measuring electrode tapping electrical potentials, especially a measuring electrode contacting flowing medium, by means of at least one measuring capacitor reacting to changes of the flow parameter, and/or by means of at least one piezoelectric and/or piezoresistive element. The flow sensor can be, especially in the case of application of a measuring capacitor and/or a piezoelectric or piezoresistive element for forming the flow sensor, one which is subjected during operation repeatedly to mechanical deformations under action of the medium flowing in the measuring system for generating the measurement signal and/or which is moved during operation repeatedly relative to a static, rest position under action of the medium flowing in the measuring tube, such as is usually the case, besides the aforementioned in-line measuring devices measuring the flow parameter on the basis of vortices entrained in the flow with formation of a Karman vortex street, e.g. also for such in-line measuring devices which measure flow parameters of the kind being discussed on the basis of pressure differences. For the latter case, the at least one flow sensor can be formed, for example, by means of at least one flow obstacle narrowing a cross section of the process line, especially an orifice plate or a nozzle, as well as by means of at least one pressure difference sensor, which registers a pressure difference arising across the flow obstacle and delivers a representative pressure difference measurement signal. The at least one pressure difference sensor can, in such case, be formed e.g. partly by means of a pressure sensor placed at the pressure measuring point. Alternatively to the aforementioned sensor- or measuring-device-types, the at least one flow sensor can, moreover, also be formed in conjunction with a line segment of the process line, wherein vibrations of such line segment, excited actively from the outside by means of an oscillation exciter and/or passively by the medium itself, are detected by means of at least one transducer element registering, for example electrodynamically or opto-electronically, mechanical oscillations and delivering a corresponding oscillation signal, such as is known to be the case, for example, also with Coriolis mass flow meters. Commercial Coriolis mass flow meters are usually in-line measuring devices, offered as compact measuring devices, in which at least one measuring tube equipped externally with oscillation exciters and sensors are inserted by means of flanges into the course of the process line to form the line segment vibrating, at least at times, during operation.

The application of measuring systems with an in-line measuring device of the aforementioned kind enables, thus, in addition to the virtually measured density, other measured variables, especially a mass flow, a volume flow, a flow velocity, a viscosity, a pressure, a temperature and/or the like, of the medium flowing in the process line equally to be ascertained highly accurately, occasionally also in real time.

At least in the case of application also of a flow sensor internal to the measuring system, it is possible, moreover, also to ascertain the above-mentioned compensation factor K directly, in advance, especially also in the course of a wet calibration. For example, compensation factor K can be very simply so selected, that the formula $$K = \Delta X \rho \cdot \frac{X_\vartheta}{X_v^2} \qquad (8)$$

is fulfilled, wherein $\Delta X \rho$ corresponds to a deviation ascertained in advance, especially in the course of a calibration of the same and/or in an essentially equal measuring system with known reference medium and/or in the course of start-up of the measuring system on-site, e.g. a calculated and/or measured, measuring-system-specific deviation, which the provisional density measured-value $X'_\rho$, ascertained for a reference medium defined at least with respect to its actual density, $\rho_{Ref}$, has from such density $\rho_{Ref}$ of the reference medium. As a result, $\Delta X \rho$ can be viewed practically also as the measurement error inherent to the measuring system, i.e. the measurement error with which the provisional density measured-value $X'_\rho$ ascertained by means of the measuring system itself is burdened at the virtual measuring point in comparison with the actual density. With knowledge of the provisional density measured-value $X'_\rho$, as well as also the actual density, $\rho_{Ref}$, of the reference medium, this measurement error can be quantified as follows:

$$\Delta X \rho = \left( \frac{X'_\rho}{\rho_{Ref}} - 1 \right), \qquad (9)$$

so that the compensation factor K, as a result, is to be so selected that it obeys, as exactly as possible, the following formula:

$$K = \Delta X \rho \cdot \frac{X_\vartheta}{X_v^2} = \left( \frac{X'_\rho}{\rho_{Ref}} - 1 \right) \cdot \frac{X_\vartheta}{X_v^2} \qquad (10)$$

Alternatively thereto or in supplementation thereof, at least in the case of application of a flow sensor internal to the measuring system, it is, however, also quite possible to ascertain the compensation factor K experimentally by means of a reference measuring system and corresponding reference media and/or by computer simulation and, based thereon, to extrapolate further numerical values for the compensation factors K for other measuring systems similar to the reference measuring system and/or to other media.

In a further embodiment of the invention, it is additionally provided that the measuring electronics, with application at least of the flow measurement signal, also ascertains a velocity measured-value $X_v$, especially a digital, velocity measured-value $X_v$, which instantaneously represents the flow velocity of the flowing medium, and/or that the measuring electronics, with application at least of the flow measurement signal, also ascertains a volume flow measured-value $X_v$, for example a digital, volume flow measured-value, which instantaneously represents a volume flow rate of the flowing medium. Alternatively thereto or in supplementation thereof, the measuring electronics, with application at least of the temperature measurement signal and the pressure measurement signal, or the density measured-value, as well as the flow measurement signal, or the volume flow measured-value derived therefrom, can, during operation, ascertain, further, a mass flow measured-value $X_m$, for example a digital, mass flow measured-value, which represents, instantaneously, a mass flow rate, or an integrated, i.e. totalized, mass flow.

For simplifying construction of the measuring system and, along therewith, for further improving accuracy of the density measured-value, the flow sensor can, in advantageous manner, be so placed that, as proposed, for example, also in U.S. Pat. Nos. 6,988,418 or 6,910,387, at least the flow measuring point and the temperature measuring point, or, as proposed, for example, also in U.S. Pat. No. 7,007,556, at least the flow measuring point and the pressure measuring point, at least partially overlap one another, especially are coincident. Alternatively thereto or in supplementation thereof, the flow measuring point can, however, also, as shown schematically in FIGS. 1 and 2, be arranged remotely from the temperature measuring point and/or the pressure measuring point, for example upstream of the temperature measuring point and/or upstream of the pressure measuring point.

In a further embodiment of the invention, it is additionally provided that the temperature sensor of the measuring system and/or the pressure sensor are, as proposed, for example, also in U.S. Pat. Nos. 6,988,418, 6,910,387 or 6,651,512, likewise provided by means of the in-line measuring device containing the flow sensor, for example an in-line measuring device in the form of a compact measuring device.

In a further embodiment of the invention, the virtual density measuring point and the flow measuring point are so selected that the medium has at the virtual density measuring point a thermodynamic state corresponding to a thermodynamic state of the medium at the velocity measuring point and/or that the medium has at the virtual density measuring point and velocity measuring point essentially equal Reynolds numbers. This can, for example, be achieved by so defining the virtual density measuring point that it and the flow measuring point at least partially overlap one another, especially are coincident. In other words, thus the density measured-value should be ascertained in such a manner that it exactly represents a local density of the medium in the region of the flow sensor and consequently also exactly represents the local density of the medium at the velocity measuring point.

For further simplifying the measuring, another embodiment of the measuring system provides that the process line is an essentially straight pipeline, thus no elbows or bends, at least sectionally, especially in the region between density measuring point and pressure measuring point and/or between density measuring point and temperature measuring point. Moreover, the process line should be embodied, at least sectionally, especially in the region of the temperature measuring point and/or in the region of the pressure measuring point, as an essentially form-stable pipeline, at least under operating pressure, especially a rigid pipeline and/or a pipeline circular in cross section.

In a further embodiment of the invention, the aforementioned variance is produced during operation in largely defined manner by providing the process line, at least at the virtual density measuring point, additionally with a caliber D1 differing from a caliber D2 of the process line at the pressure measuring point. Alternatively thereto or in supplementation thereof, another embodiment of the invention additionally provides that the process line has at the virtual density measuring location a caliber D1 differing from caliber D3 of the process line at the temperature measuring point, and/or that the caliber D2 of the process line at the pressure measuring point is different from the caliber D3 of the process line at the temperature measuring point. In detail, thus, a large number of possibilities of combination results as regards the arrangement of the individual measuring points relative to one another, as well as also the choice of caliber of the process line at the particular measuring points. A selection of especially suited variants of embodiment herefor is, moreover, also shown schematically in FIGS. 4a, 4b, 4c, 4d, 4e, 4f and 4h.

As shown therein, it can be of advantage to embody the measuring system such that the caliber D2 of the process line is greater at the pressure measuring point than the caliber D3 of the process line at the temperature measuring point, or, however, also such that the caliber D3 of the process line at the temperature measuring point is greater than the caliber D2 of the process line at the pressure measuring point. Alternatively thereto or in supplementation thereof, the caliber D2 of the process line at the pressure measuring point can also be so selected that it is greater than the caliber D1 of the process line at the virtual density measuring point and/or the caliber D3 of the process line at the temperature measuring point can be so selected that it is greater than the caliber D1 at the virtual density measuring point. Especially, it is further provided that a caliber ratio D3/D1 of the caliber D3 of the process line at the temperature measuring point to the caliber D1 of the process line at the virtual density measuring point is greater than 1.1 and/or smaller than 5, for example thus lying in a range between 1.2 and 3.1. Further, it is at least for this case, of advantage when the process line at the virtual density measuring point has a caliber D1, which is essentially equal to a caliber D2 of the process line at the temperature measuring point. In another embodiment of the invention, it is provided that a caliber ratio D2/D1 of the caliber D2 of the process line at the pressure measuring point to the caliber D1 of the process line at the virtual density measuring point is kept greater than 1.1 and/or smaller than 5, for example thus lying in a range between 1.2 and 3.1. For this case it is, in turn, of advantage when the process line at the virtual density measuring point has a caliber D1, which is essentially equal to a caliber D3 of the process line at the temperature measuring point.

The differences between the calibers D1, D2, D3, respectively, can, depending on desired configuration, be implemented by providing the process line between at least two of the aforementioned measuring points, for example thus between the virtual density measuring point and the temperature measuring point and/or the pressure measuring point, or also between the temperature measuring point and the pressure measuring point, with a line segment embodied as a diffuser, especially a funnel-shaped diffuser, having a lumen widening in the flow direction, especially continuously widening in the flow direction, or a line segment which is formed as a nozzle, especially a funnel-shaped nozzle having a lumen narrowing in the flow direction, especially continuously narrowing in the flow direction.

Experimental investigations have shown further that the measuring points should, in advantageous manner, be so placed, or defined, that a distance L21 of the pressure measuring point from the virtual density measuring point differs from a distance L31 of the temperature measuring point from the virtual density measuring point. For example, it can be quite advantageous for the measurement, when the distance L21 of the pressure measuring point from the virtual density measuring point is greater than the distance L31 of the temperature measuring point from the virtual density measuring point and/or when the distance L21 of the pressure measuring point from the virtual density measuring point and/or a distance L23 of the pressure measuring point from the temperature measuring point are/is greater than the caliber D2 of the process line at the pressure measuring point. Found to be quite suitable are, in such case, a distance L21 and/or a distance L23 of at least three times, especially more than five times, the caliber D2.

Further information for layout and dimensioning of the process line of the measuring system as regards aforementioned installed lengths and/or caliber ratios in the case of application of a reducer are and/or a diffuser, as well as also other embodiments of the process line upstream of the flow sensor and or downstream of the flow of sensor are hereby explicitly referenced in the assignee's not-prepublished applications DE 102006034296.8 und 102006047815.0, or in subsequent applications corresponding therewith, whose respective disclosures are thus to be considered as belonging to the present application.

Further investigations with measuring systems of the invention have shown additionally for the arrangements of temperature, pressure and density measuring-points shown in the FIGS. 4a, 4b, 4c, 4d relative to one another as well as with reference to the aforementioned caliber ratios, that that the density correction value ascertained therefor at least according to formula (4) and used for the ascertaining of the density measured-value according to the formula (1), or (2), should always be greater than one; otherwise, as already mentioned, a malfunctioning measuring system or a disturbance of the plant would be assumed. Equally, for the constellations shown in FIGS. 4e, 4f, 4g, and 4h, the density correction value, assuming application of the same calculative formulas, should always be smaller than one.

Figure 2:
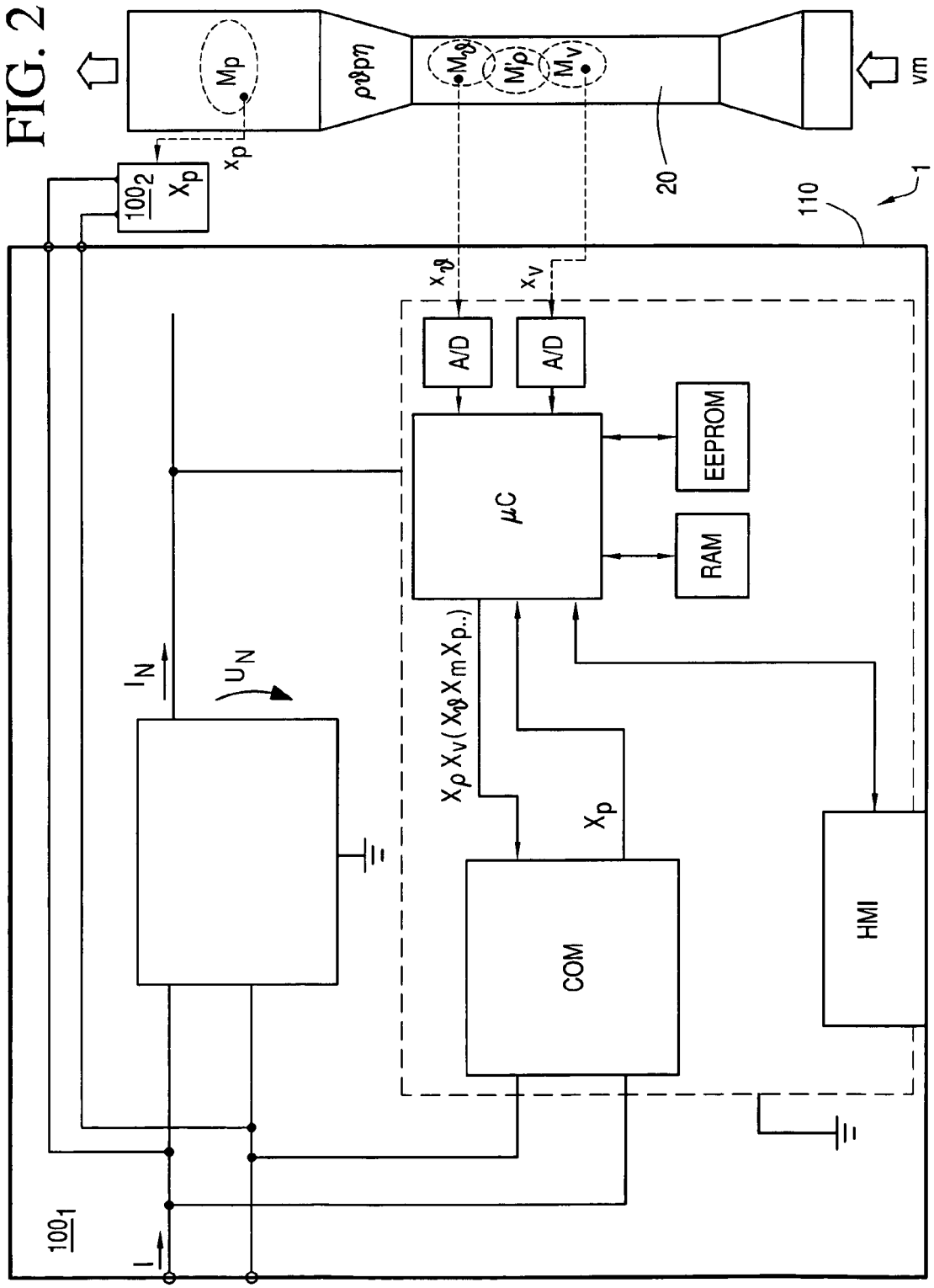
FIG. 2 the measuring system of FIG. 1, this time in the form of a block diagram.

Beyond this, the following Table 1 provides constellations as regards calibers D1, D2, D3, in each case in the units mm, and selected gases as medium, as well as in each case a correspondingly suitable compensation factor K in the units $K \cdot s^2 \cdot m^{-2}$, especially suitable for a measuring system with a flow sensor according to the example of an embodiment shown in FIGS. 2 and 3.

TABLE 1

| GAS | D1, D3 | D2 | K |
|---|---|---|---|
| $CH_4$ | 13.9 | 24.3 | 27851.08558 |
| ($n = 16$ g · mol$^{-1}$, | 13.9 | 26.7 | 26084.12357 |
| $f = 6$) | 13.9 | 27.2 | 25671.22129 |
|  | 13.9 | 28.5 | 24567.65186 |
|  | 13.9 | 38.1 | 17069.51792 |
|  | 13.9 | 40.9 | 15350.28348 |
|  | 13.9 | 41.2 | 15178.90947 |
|  | 13.9 | 43.1 | 14147.85441 |
|  | 24.3 | 38.1 | 3086.763684 |
|  | 24.3 | 40.9 | 3035.482335 |
|  | 24.3 | 41.2 | 3026.384008 |
|  | 24.3 | 43.1 | 2957.410639 |
|  | 24.3 | 49.2 | 2662.97974 |
|  | 24.3 | 52.6 | 2484.170531 |
|  | 24.3 | 52.7 | 2478.934254 |
|  | 24.3 | 54.5 | 2385.462689 |
|  | 38.1 | 49.2 | 448.2000215 |
|  | 38.1 | 52.6 | 487.9209744 |
|  | 38.1 | 54.5 | 500.3838513 |
|  | 38.1 | 73.7 | 459.369374 |
|  | 38.1 | 78 | 435.8925863 |
|  | 38.1 | 78.1 | 435.337907 |
|  | 38.1 | 82.5 | 410.9043438 |
|  | 49.2 | 73.7 | 183.0929623 |
|  | 49.2 | 78 | 183.4977725 |

TABLE 1-continued

| GAS | D1, D3 | D2 | K |
|---|---|---|---|
|  | 49.2 | 78.1 | 183.4687956 |
|  | 49.2 | 82.5 | 180.8940523 |
|  | 49.2 | 97 | 162.4571647 |
|  | 49.2 | 102.3 | 154.3167919 |
|  | 49.2 | 102.4 | 154.1619225 |
|  | 49.2 | 107.1 | 146.8997624 |
|  | 73.7 | 97 | 32.98911974 |
|  | 73.7 | 102.4 | 35.0370316 |
|  | 73.7 | 107.1 | 36.01526944 |
|  | 73.7 | 146 | 32.12475476 |
|  | 73.7 | 151 | 31.10798557 |
|  | 73.7 | 154.2 | 30.45138942 |
|  | 73.7 | 159.3 | 29.40598339 |
|  | 97 | 146 | 12.12975471 |
|  | 97 | 151 | 12.16106709 |
|  | 97 | 154.2 | 12.14098846 |
|  | 97 | 159.3 | 12.05687371 |
|  | 97 | 199.9 | 10.30674712 |
|  | 97 | 202.7 | 10.16121596 |
|  | 97 | 206.5 | 9.963705636 |
|  | 97 | 207.3 | 9.922187549 |
|  | 146 | 199.9 | 2.245529752 |
|  | 146 | 202.7 | 2.273600656 |
|  | 146 | 206.5 | 2.304852917 |
|  | 146 | 207.3 | 2.310502276 |
|  | 146 | 248.8 | 2.317268815 |
|  | 146 | 254.5 | 2.291734778 |
|  | 146 | 258.8 | 2.2702775 |
|  | 146 | 260.4 | 2.261877863 |
| Natural gas | 13.9 | 24.3 | 31170.01324 |
| ($n = 16 \ldots 40$ g · mol$^{-1}$, | 13.9 | 26.7 | 29190.34938 |
| depending on composition, | 13.9 | 27.2 | 28727.93943 |
| $f = 6$) | 13.9 | 28.5 | 27492.24479 |
|  | 13.9 | 38.1 | 19099.80535 |
|  | 13.9 | 40.9 | 17175.91318 |
|  | 13.9 | 41.2 | 16984.14311 |
|  | 13.9 | 43.1 | 15830.39114 |
|  | 24.3 | 38.1 | 3455.020015 |
|  | 24.3 | 40.9 | 3397.337203 |
|  | 24.3 | 41.2 | 3387.128821 |
|  | 24.3 | 43.1 | 3309.793458 |
|  | 24.3 | 49.2 | 2980.007098 |
|  | 24.3 | 52.6 | 2779.822049 |
|  | 24.3 | 52.7 | 2773.96038 |
|  | 24.3 | 54.5 | 2669.329455 |
|  | 38.1 | 49.2 | 501.8495813 |
|  | 38.1 | 52.6 | 546.2444885 |
|  | 38.1 | 54.5 | 560.159696 |
|  | 38.1 | 73.7 | 514.0710105 |
|  | 38.1 | 78 | 487.7826811 |
|  | 38.1 | 78.1 | 487.1616486 |
|  | 38.1 | 82.5 | 459.8077209 |
|  | 49.2 | 73.7 | 204.9496071 |
|  | 49.2 | 78 | 205.3864268 |
|  | 49.2 | 78.1 | 205.3536589 |
|  | 49.2 | 82.5 | 202.458931 |
|  | 49.2 | 97 | 181.8004079 |
|  | 49.2 | 102.3 | 172.6858252 |
|  | 49.2 | 102.4 | 172.5124389 |
|  | 49.2 | 107.1 | 164.3825333 |
|  | 73.7 | 97 | 36.93625048 |
|  | 73.7 | 102.4 | 39.22468158 |
|  | 73.7 | 107.1 | 40.31654938 |
|  | 73.7 | 146 | 35.94964274 |
|  | 73.7 | 151 | 34.81116896 |
|  | 73.7 | 154.2 | 34.07605503 |
|  | 73.7 | 159.3 | 32.90573249 |
|  | 97 | 146 | 13.57764009 |
|  | 97 | 151 | 13.61203427 |
|  | 97 | 154.2 | 13.58918743 |
|  | 97 | 159.3 | 13.49451405 |
|  | 97 | 199.9 | 11.53365739 |
|  | 97 | 202.7 | 11.37072445 |
|  | 97 | 206.5 | 11.14960825 |
|  | 97 | 207.3 | 11.10312955 |
|  | 146 | 199.9 | 2.5139906 |
|  | 146 | 202.7 | 2.545346756 |
|  | 146 | 206.5 | 2.580243371 |

TABLE 1-continued

| GAS | D1, D3 | D2 | K |
|---|---|---|---|
|  | 146 | 207.3 | 2.586549405 |
|  | 146 | 248.8 | 2.593473866 |
|  | 146 | 254.5 | 2.564840534 |
|  | 146 | 258.8 | 2.540788021 |
|  | 146 | 260.4 | 2.531374101 |
| $H_2O$ ($n = 18$ g·mol$^{-1}$, $f = 6$) | 13.9 | 24.3 | 31256.24144 |
|  | 13.9 | 26.7 | 29271.0454 |
|  | 13.9 | 27.2 | 28807.34836 |
|  | 13.9 | 28.5 | 27568.21927 |
|  | 13.9 | 38.1 | 19152.54293 |
|  | 13.9 | 40.9 | 17223.33422 |
|  | 13.9 | 41.2 | 17031.03432 |
|  | 13.9 | 43.1 | 15874.09507 |
|  | 24.3 | 38.1 | 3464.588763 |
|  | 24.3 | 40.9 | 3406.738816 |
|  | 24.3 | 41.2 | 3396.501521 |
|  | 24.3 | 43.1 | 3318.948505 |
|  | 24.3 | 49.2 | 2988.242826 |
|  | 24.3 | 52.6 | 2787.502227 |
|  | 24.3 | 52.7 | 2781.624305 |
|  | 24.3 | 54.5 | 2676.703394 |
|  | 38.1 | 49.2 | 503.2441144 |
|  | 38.1 | 52.6 | 547.7602846 |
|  | 38.1 | 54.5 | 561.7131315 |
|  | 38.1 | 73.7 | 515.492087 |
|  | 38.1 | 78 | 489.1306726 |
|  | 38.1 | 78.1 | 488.5079154 |
|  | 38.1 | 82.5 | 461.07809 |
|  | 49.2 | 73.7 | 205.5175663 |
|  | 49.2 | 78 | 205.9551717 |
|  | 49.2 | 78.1 | 205.9223044 |
|  | 49.2 | 82.5 | 203.0192259 |
|  | 49.2 | 97 | 182.3029139 |
|  | 49.2 | 102.3 | 173.1630088 |
|  | 49.2 | 102.4 | 172.9891412 |
|  | 49.2 | 107.1 | 164.8366844 |
|  | 73.7 | 97 | 37.03884498 |
|  | 73.7 | 102.4 | 39.33351491 |
|  | 73.7 | 107.1 | 40.42832654 |
|  | 73.7 | 146 | 36.04900682 |
|  | 73.7 | 151 | 34.90736955 |
|  | 73.7 | 154.2 | 34.1702149 |
|  | 73.7 | 159.3 | 32.99664598 |
|  | 97 | 146 | 13.61526406 |
|  | 97 | 151 | 13.64973647 |
|  | 97 | 154.2 | 13.62681665 |
|  | 97 | 159.3 | 13.53186744 |
|  | 97 | 199.9 | 11.56552973 |
|  | 97 | 202.7 | 11.40214452 |
|  | 97 | 206.5 | 11.18041482 |
|  | 97 | 207.3 | 11.1338072 |
|  | 146 | 199.9 | 2.52096787 |
|  | 146 | 202.7 | 2.552409208 |
|  | 146 | 206.5 | 2.587400279 |
|  | 146 | 207.3 | 2.593723327 |
|  | 146 | 248.8 | 2.600650057 |
|  | 146 | 254.5 | 2.571936044 |
|  | 146 | 258.8 | 2.547815996 |
|  | 146 | 260.4 | 2.538375687 |
| Air ($n = 29$ g·mol$^{-1}$, $f = 5$) | 13.9 | 24.3 | 50338.90921 |
|  | 13.9 | 26.7 | 47124.38089 |
|  | 13.9 | 27.2 | 46375.14885 |
|  | 13.9 | 28.5 | 44374.58191 |
|  | 13.9 | 38.1 | 30815.23069 |
|  | 13.9 | 40.9 | 27710.05332 |
|  | 13.9 | 41.2 | 27400.56851 |
|  | 13.9 | 43.1 | 25538.71377 |
|  | 24.3 | 38.1 | 5583.208016 |
|  | 24.3 | 41.2 | 5470.96068 |
|  | 24.3 | 43.1 | 5344.897321 |
|  | 24.3 | 49.2 | 4810.117614 |
|  | 24.3 | 52.6 | 4486.285526 |
|  | 24.3 | 52.7 | 4476.808075 |
|  | 24.3 | 54.5 | 4307.671069 |
|  | 38.1 | 49.2 | 812.4565419 |
|  | 38.1 | 52.6 | 883.65719 |
|  | 38.1 | 54.5 | 905.8569033 |
|  | 38.1 | 73.7 | 829.8882553 |
|  | 38.1 | 78 | 787.3215533 |
|  | 38.1 | 78.1 | 786.316573 |
|  | 38.1 | 82.5 | 742.0716954 |
|  | 49.2 | 73.7 | 331.3026455 |
|  | 49.2 | 78 | 331.8738927 |
|  | 49.2 | 78.1 | 331.8181848 |
|  | 49.2 | 82.5 | 327.0348906 |
|  | 49.2 | 97 | 293.4714706 |
|  | 49.2 | 102.3 | 278.7184046 |
|  | 49.2 | 102.4 | 278.437899 |
|  | 49.2 | 107.1 | 265.289832 |
|  | 73.7 | 97 | 59.78309893 |
|  | 73.7 | 102.4 | 63.449488 |
|  | 73.7 | 107.1 | 65.18836646 |
|  | 73.7 | 146 | 58.03092489 |
|  | 73.7 | 151 | 56.18799037 |
|  | 73.7 | 154.2 | 54.9986214 |
|  | 73.7 | 159.3 | 53.10590103 |
|  | 97 | 146 | 21.94754221 |
|  | 97 | 151 | 21.99771435 |
|  | 97 | 154.2 | 21.95771667 |
|  | 97 | 159.3 | 21.80041304 |
|  | 97 | 199.9 | 18.61596382 |
|  | 97 | 202.7 | 18.35235887 |
|  | 97 | 206.5 | 17.99471318 |
|  | 97 | 207.3 | 17.91954828 |
|  | 146 | 199.9 | 4.067220274 |
|  | 146 | 202.7 | 4.117361285 |
|  | 146 | 206.5 | 4.173054129 |
|  | 146 | 207.3 | 4.183100739 |
|  | 146 | 248.8 | 4.188923875 |
|  | 146 | 254.5 | 4.142218763 |
|  | 146 | 258.8 | 4.103061713 |
|  | 146 | 260.4 | 4.087749585 |

The invention claimed is:

1. A measuring system for measuring a density of a medium being variable as regards a thermodynamic state flowing in a process line along a flow axis of the measuring system, said measuring system comprising:
at least one temperature sensor placed at a temperature measuring point, said temperature sensor reacting to a local temperature of a medium flowing past, and said temperature sensor delivering at least one temperature measurement signal influenced by the local temperature of the medium;
at least one pressure sensor placed at a pressure measuring point, said pressure sensor reacting to a local pressure of the medium flowing past, and said pressure sensor delivering at least one pressure measurement signal influenced by the local pressure in the medium; and
a measuring electronics communicating, with at least the temperature sensor and with the pressure sensor, said measuring electronics calculating, with application of the temperature measurement signal and at least the pressure measurement signal, at least one density measured-value representing, instantaneously, a local density of the flowing medium at a virtual density measuring point predetermineably spaced from the pressure measuring point along the flow axis and/or predetermineably spaced from the temperature measuring point along the flow axis, and said measuring electronics communicating with a superordinated, electronic, data processing system; wherein:
said measuring electronics transmits the density measured-value to the data processing system and
the measuring electronics receives from said data processing system, at least at times, numerical parameter values for the measuring system parameter specifying medium currently to be measured, said measuring system parameter being selected from a group consisting of: thermodynamic properties of said medium currently to be measured, chemical composition of said medium currently to be measured, a specific heat capacity, $c_p$, of said medium currently to be measured, a molar mass, n, of said medium currently to be measured, and a number, f, of oscillatory degrees of freedom of the atoms or molecules of said medium currently to be measured.

2. The measuring system as claimed in claim 1, wherein: said measuring electronics includes non-volatile data memory, which stores, at least one measuring system parameter specifying.

3. The measuring system as claimed in claim 1, wherein: said measuring electronics ascertains, with application of the at least one measuring system parameter ($SP_M$) specifying the density measured-value ($X_\rho$).

4. The measuring system as claimed in claim 1, wherein: said measuring electronics includes a non-volatile data memory, which stores, a measuring system parameter specifying the medium by means of the measuring system for instantaneous circumstances of installation of the measuring system; and the circumstances of installation are determined by the arrangement of pressure-, temperature- and density-measuring points relative to one another, and in each case, by form and size of the process line in the region of the pressure-, density- and/or temperature-measuring points.

5. The measuring system as claimed in claim 4, wherein: said measuring electronics ascertains the density measured-value with application of the at least one measuring system parameter specifying both the medium by means of the measuring system and instantaneous circumstances of installation of the measuring system.

6. a measuring system for measuring a density of a medium being variable as regards a thermodynamic state flowing in a process line along a flow axis of the measuring system, said measuring system comprising:

at least one temperature sensor placed at a temperature measuring point, said temperature sensor reacting to a local temperature of a medium flowing past, and said temperature sensor delivering at least one temperature measurement signal influenced by the local temperature of the medium;

at least one pressure sensor placed at a pressure measuring point, said pressure sensor reacting to a local pressure of the medium flowing past, and said pressure sensor delivering at least one pressure measurement signal influenced by the local pressure in the medium; and a measuring electronics communicating with at least the temperature sensor and with the pressure sensor, and calculating, at least at times, with application of the temperature measurement signal and at least the pressure measurement signal, at least one density measured-value representing, instantaneously, a local density of the flowing medium at a virtual density measuring point predeterminably spaced from the pressure measuring point along the flow axis and/or predeterminably spaced from the temperature measuring point along the flow axis, wherein:

said measuring electronics includes a non-volatile data memory, which stores, at least one measuring system parameter of a first kind currently specifying the medium further stores, at least one measuring system parameter of a second kind specifying both the medium and instantaneous circumstances of installation of the measuring system; which are determined by the arrangement of pressure-, temperature- and pressure-measuring points relative to one another, which are determined by form and size of the process line in the region of the pressure-, density-, and/or temperature-measuring points, and said measuring electronics ascertains the density measured-value with application at least of the measuring system parameter of the first kind and the measuring system parameter of the second kind.

7. The measuring system as claimed in claim 1, wherein said measuring electronics communicates via a fieldbus with said superordinated, electronic, data processing system; and/or wherein said measuring electronics communicates by wire with said superordinated, electronic, data processing system; and/or wherein said measuring electronics communicates by radio, with said superordinated, electronic, data processing system.

8. The measuring system as claimed in claim 1, wherein: said measuring electronics is connected with the superordinated electronic data processing system by means of a fieldbus.

9. A measuring system for measuring a density of a medium being variable as regards a thermodynamic state flowing in a process line along a flow axis of the measuring system, said measuring system comprising:

at least one temperature sensor placed at a temperature measuring point, said temperature sensor reacting to a local temperature of a medium flowing past, and said temperature sensor delivering at least one temperature measurement signal influenced by the local temperature of the medium;

at least one pressure sensor placed at a pressure measuring point, said pressure sensor reacting to a local pressure of the medium flowing past, and said pressure sensor delivering at least one pressure measurement signal influenced by the local pressure in the medium; and a measuring electronics communicating with at least the temperature sensor and with the pressure sensor, and calculating, with application of the temperature measurement signal and at least the pressure measurement signal, at least one density measured-value representing, instantaneously, a local density of the flowing medium at a virtual density measuring point predeterminably spaced from the pressure measuring point along the flow axis and/or predeterminably spaced from the temperature measuring point along the flow axis, wherein: said measuring electronics ascertains during operation, a specific heat capacity, $c_p$, of the medium currently to be measured.

10. The measuring system as claimed in claim 1, wherein: said measuring electronics repetitively generates, based on the temperature measurement signal, a temperature measured-value ($X_\Theta$) representing, instantaneously, a local temperature of the medium at the temperature measuring point.

11. The measuring system as claimed in claim 1, wherein: said measuring electronics generates repetitively, based on the pressure measurement signal, a pressure measurement signal ($X_p$) representing, instantaneously, a pressure reigning in the medium at the pressure measuring point.

12. The measuring system as claimed in claim 1, further comprising: at least one flow sensor placed at a flow measuring point, reacting to a local flow parameter and delivering at least one flow measurement signal influenced by the local flow parameter.

13. The measuring system as claimed in claim 12, wherein: said measuring electronics communicates with the flow sensor; and said measuring electronics ascertains, with application also of the flow measurement signal, the density measured-value.

14. The measuring system as claimed in claim 12, wherein: the medium shows at the virtual density measuring point a thermodynamic state corresponding to a thermodynamic state of the medium at the velocity measuring point.

15. The measuring system as claimed in claim 12, wherein: the virtual density measuring point and the flow measuring point at least partially overlap one another.

16. The measuring system as claimed in claim 12, wherein: the temperature measuring point and the flow measuring point overlap one another at least partially.

17. The measuring system as claimed in claim 12, wherein: the pressure measuring point and the flow measuring point at least partially overlap.

18. The measuring system as claimed in claim 12, wherein: the density measured-value represents a local density of the medium in the region of the flow sensor.

19. The measuring system as claimed in claim 12, wherein: said measuring electronics communicates with the flow sensor by means of a fieldbus and/or wirelessly by radio.

20. The measuring system as claimed in claim 12, wherein: said measuring electronics communicates with the flow sensor; and said measuring electronics, with application at least of the flow measurement signal, ascertains a velocity measured-value $(X_v)$ representing, instantaneously, the flow velocity of the flowing medium.

21. A measuring system for measuring a density of a medium being variable as regards a thermodynamic state flowing in a process line along a flow axis of the measuring system, said measuring system comprising:
at least one temperature sensor placed at a temperature measuring point, said temperature sensor reacting to a local temperature of a medium flowing past, and said temperature sensor delivering at least one temperature measurement signal influenced by the local temperature of the medium;
at least one pressure sensor placed at a pressure measuring point, said pressure sensor reacting to a local pressure of the medium flowing past, and said pressure sensor delivering at least one pressure measurement signal influenced by the local pressure in the medium; and
a measuring electronics communicating with at least the temperature sensor and with the pressure sensor, and calculating, at least at times, with application of the temperature measurement signal and at least the pressure measurement signal, at least one density measured-value $(X_\rho)$ representing, instantaneously, a local density of the flowing medium at a virtual density measuring point predeterminably spaced from the pressure measuring point along the flow axis and/or predeterminably spaced from the temperature measuring point along the flow axis, wherein:
said measuring electronics produces the density measured-value, also with application of at least one numerical compensation factor (K), which corresponds with a spatial variance of at least one thermodynamic variable of the medium, said spatial variance occurring along the flow axis of the measuring system, and/or which, corresponds with a spatial variance of the Reynolds number of the flowing medium along the flow axis of the measuring system.

22. The measuring system as claimed in claim 21, wherein: the at least one compensation factor (K) is ascertained taking into consideration the medium.

23. The measuring system as claimed in claim 22, wherein: said measuring electronics ascertains the at least one compensation factor (K) at least once during start-up of the measuring system, and/or said measuring electronics ascertains the compensation factor (K) repetitively during operation of the measuring system.

24. The measuring system as claimed in claim 23, wherein: said measuring electronics ascertains the at least one compensation factor (K) on the basis of a predetermined, specific heat capacity, $c_p$, of the current medium.

25. Measuring system as claimed in claim 21, wherein the measuring electronics includes a data memory, embodied as a table memory and/or embodied as a non-volatile memory, storing the at least one compensation factor (K).

26. The measuring system as claimed in claim 25, wherein: the data memory stores a plurality of compensation factors ascertained in advance for different media and/or for different circumstances of installation.

27. The measuring system as claimed in claim 26, wherein: said measuring electronics selects the at least one compensation factor (K) from a plurality of compensation factors stored in the data memory, taking into consideration the current medium, and the current circumstances of installation.

28. A measuring system for measuring a density of a medium being variable as regards a thermodynamic state flowing in a process line along a flow axis of the measuring system, said measuring system comprising:
at least one temperature sensor placed at a temperature measuring point, said temperature sensor reacting to a local temperature of a medium flowing past, and said temperature sensor delivering at least one temperature measurement signal influenced by the local temperature of the medium;
at least one pressure sensor placed at a pressure measuring point, said pressure sensor reacting to a local pressure of the medium flowing past, and said pressure sensor delivering at least one pressure measurement signal influenced by the local pressure in the medium; and
a measuring electronics communicating with at least the temperature sensor and with the pressure sensor, and calculating, at least at times, with application of the temperature measurement signal and at least the pressure measurement signal, at least one density measured-value $(X_\rho)$ representing, instantaneously, a local density of the flowing medium at a virtual density measuring point predeterminably spaced from the pressure measuring point along the flow axis and/or predeterminably spaced from the temperature measuring point along the flow axis, wherein:
said measuring electronics produces the density measured-value $(X_\rho)$ with application of at least one density correction value $(X_K)$ ascertained at run time, said density correction value depending on both, a flow velocity of the medium and a local temperature reigning at the temperature measuring point and said density correction value corresponding with an instantaneous spatial variance of at least one thermodynamic state variable of the medium with an instantaneous spatial variance of the Reynolds number of the flowing medium.

29. The measuring system as claimed in claim 28 wherein: said measuring electronics ascertains the density correction value ($X_K$) with application of the velocity measured-value ($X_v$) and the temperature measured-value ($X_\Theta$).

30. The measuring system as claimed in claim 21, wherein: said measuring electronics ascertains the density correction value ($X_K$) also with application of the at least one compensation factor (K) ascertained in advance.

31. The measuring system as claimed in claim 28, wherein: said measuring electronics compares the density correction value ($X_K$) repetitively during operation with at least one predetermined, reference value.

32. The measuring system as claimed in claim 31, wherein: said measuring electronics, based on the comparison of density correction value ($X_K$) and reference value, quantitatively signals an instantaneous deviation of the density correction value ($X_K$) from the reference value and/or generates, at times, an alarm signaling an undesired discrepancy between density correction value ($X_K$) and associated reference value.

33. A measuring system for measuring a density of a medium being variable as regards a thermodynamic state flowing in a process line along a flow axis of the measuring system, said measuring system comprising:
at least one temperature sensor placed at a temperature measuring point, said temperature sensor reacting to a local temperature of a medium flowing past, and said temperature sensor delivering at least one temperature measurement signal influenced by the local temperature of the medium;
at least one pressure sensor placed at a pressure measuring point, said pressure sensor reacting to a local pressure of the medium flowing past, and said pressure sensor delivering at least one pressure measurement signal influenced by the local pressure in the medium; and
a measuring electronics communicating with at least the temperature sensor and with the pressure sensor, and calculating, at least at times, with application of the temperature measurement signal and at least the pressure measurement signal, at least one density measured-value ($X_{92}$) representing, instantaneously, a local density of the flowing medium at a virtual density measuring point predeterminably spaced from the pressure measuring point along the flow axis and/or predeterminably spaced from the temperature measuring point along the flow axis, wherein:
said measuring electronics, based on the pressure measurement signal, the temperature measurement signal and based on the formula:

$$X'_\rho = \frac{n}{z \cdot R_M} \cdot \frac{X_p}{X_\vartheta},$$

ascertains a provisional density measured-value ($X'_\rho$.) representing a density which the flowing medium only apparently shows at the virtual density measuring point, where n is a molar mass, z is a real gas factor of the medium, and $R_M$ is a relative gas constant of the medium to be measured, corresponding with absolute the gas constant R/n normalized with the molar mass n of the medium, with R=8.3143 J/(K mol).

34. The measuring system as claimed in claim 33, wherein: said measuring electronics ascertains, repetitively during operation, a density error corresponding with a deviation between the provisional density measured value ($X'_\rho$) and the density measured-value ($X_\rho$).

35. The measuring system as claimed in claim 34, wherein: said measuring electronics outputs a numerical density error value representing said instantaneous density error and/or compares the instantaneous density error with at least one, predetermined, reference value, and, based on this comparison, generates, at times, an alarm signaling an undesired discrepancy between the provisional density measured-value and the density measured-value.

36. The measuring system as claimed in claim 33, wherein: said measuring electronics ascertains the density measured-value ($X_\rho$) with application both of the provisional density measured-value ($X'_\rho$) and also the density correction value ($X_K$).

37. The measuring system as claimed in claim 36, wherein: said measuring electronics applies the density correction value ($X_K$) in generating the density measured-value ($X_\rho$), solely when it lies in a range between 1 and 1.2.

38. The measuring system as claimed in claim 36, wherein: said measuring electronics applies the density correction value ($X_K$) in generating the density measured-value ($X_\rho$), solely when it lies in a range between 0.8 and 1.

39. The measuring system as claimed in claim 33, wherein: the compensation factor (K) is so selected that it fulfills the following formula:

$$K = \Delta X \rho \cdot \frac{X_\vartheta}{X_v^2},$$

where $\Delta X\rho$ is a measuring system specific deviation, which the provisional density measured-value ($X'_\rho$), ascertained for a reference medium defined at least as regards its actual density, $\rho_{Ref}$, shows from the same density, $\rho_{Ref}$, of the reference medium, and which is ascertained in advance in the course of a calibration of the measuring system and/or of a measuring system of essentially equal type with known reference medium and/or in the course of startup of the measuring system on-site.

40. The measuring system as claimed in claim 39, wherein: the compensation factor (K) fulfills the following formula:

$$K = \Delta X \rho \cdot \frac{X_\vartheta}{X_v^2} = \left(\frac{X'_\rho}{\rho_{Ref}} - 1\right) \cdot \frac{X_\vartheta}{X_v^2}.$$

41. The measuring system as claimed in claim 21, further comprising:
at least one flow sensor communicating with the measuring electronics, placed at a flow measuring point, and reacting primarily to a local flow parameter of the medium to be measured, wherein: said flow sensor delivers at least one flow measurement signal influenced by the local flow parameter; said measuring electronics, with application at least of the flow measurement signal, generates a velocity measured signal ($X_v$), which represents, instantaneously, the flow velocity of the flowing medium, as well as, generates based on the temperature measurement signal, a temperature measured-value ($X_\Theta$), which represents, instantaneously, a local temperature of the medium; and said measuring electronics ascertains the density measured-value ($X_\rho$), at least at times, based on the formula:

$$X_\rho = \frac{n \cdot X_p}{z \cdot R_M \cdot (X_\vartheta + K \cdot X_v^2)} = \frac{n \cdot X_p}{z \cdot R_M \cdot X_\vartheta} \cdot \frac{1}{\left(1 + K \cdot \frac{X_v^2}{X_\vartheta}\right)}$$

where n is a molar mass, z is a real gas factor of the medium, and $R_M$ is a relative gas constant of the medium to be measured, corresponding with the absolute gas constant normalized with the molar mass n of the medium, thus R/n, with R is equal to 8.3143 J/(K mol).

42. A measuring system for measuring a density of a medium being variable as regards a thermodynamic state flowing in a process line along a flow axis of the measuring system, said measuring system comprising:
   at least one temperature sensor placed at a temperature measuring point, said temperature sensor reacting to a local temperature of a medium flowing past, and said temperature sensor delivering at least one temperature measurement signal influenced by the local temperature of the medium;
   at least one pressure sensor placed at a pressure measuring point, said pressure sensor reacting to a local pressure of the medium flowing past, and said pressure sensor delivering at least one pressure measurement signal influenced by the local pressure in the medium;
   at least one flow sensor placed at a flow measuring point, reacting to a local flow parameter and delivering at least one flow measurement signal influenced by the local flow parameter; and
   a measuring electronics communicating with the temperature sensor, with the pressure sensor, and with the flow sensor, said measuring electronics calculating, at least at times, with application of the temperature measurement signal and at least the pressure measurement signal, at least one density measured-value representing, instantaneously, a local density of the flowing medium at a virtual density measuring point predeterminably spaced from the pressure measuring point along the flow axis and/or predeterminably spaced from the temperature measuring point along the flow axis, and said measuring electronics, with application at least of the flow measurement signal, ascertaining a volume flow measured-value ($X_v$) instantaneously representing a volume flow rate of the flowing medium.

43. The measuring system as claimed in claim 42, wherein: said measuring electronics, with application at least of the density measured-value and the volume flow measured-value ascertains a mass flow measured-value ($X_m$) representing, instantaneously, a mass flow rate of the flowing medium.

44. The measuring system as claimed in claim 12, wherein: said measuring electronics, with application at least of the temperature measurement signal, the pressure measurement signal and the flow measurement signal, ascertains a mass flow measured-value representing, instantaneously, a mass flow rate of the flowing medium.

45. The measuring system as claimed in claim 12, wherein: the flow measuring point is located upstream of the temperature measuring point and/or upstream of the pressure measuring point.

46. The measuring system as claimed in claim 1, wherein: the virtual density measuring point is locationally fixed.

47. Use of the measuring system as claimed in claim 1 for measuring a density of a compressible medium flowing in a process line.

\* \* \* \* \*